US012593977B2

(12) United States Patent
Hunter et al.

(10) Patent No.: US 12,593,977 B2
(45) Date of Patent: Apr. 7, 2026

(54) VISION SCREENING DEVICE INCLUDING COLOR IMAGING

(71) Applicant: Welch Allyn, Inc., Skaneateles Falls, NY (US)

(72) Inventors: Vivian Loomis Hunter, Auburn, NY (US); David L. Kellner, Baldwinsville, NY (US); James Brendan Cappon, Rochester, NY (US); John A. Lane, Venice, FL (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 374 days.

(21) Appl. No.: 18/099,062

(22) Filed: Jan. 19, 2023

(65) Prior Publication Data

US 2023/0233078 A1 Jul. 27, 2023

Related U.S. Application Data

(60) Provisional application No. 63/301,667, filed on Jan. 21, 2022.

(51) Int. Cl.
*A61B 3/14* (2006.01)
*A61B 3/00* (2006.01)
*A61B 3/12* (2006.01)

(52) U.S. Cl.
CPC .............. *A61B 3/14* (2013.01); *A61B 3/0008* (2013.01); *A61B 3/12* (2013.01)

(58) Field of Classification Search
CPC ......... A61B 3/0008; A61B 3/032; A61B 3/10; A61B 3/12; A61B 3/14
See application file for complete search history.

(56) References Cited

U.S. PATENT DOCUMENTS

| | | | |
|---|---|---|---|
| 7,878,652 B2 | 2/2011 | Chen et al. | |
| 9,332,901 B2 | 5/2016 | Eraluoto | |

(Continued)

FOREIGN PATENT DOCUMENTS

| | | |
|---|---|---|
| CN | 202981958 U | 6/2013 |
| CN | 112669357 A | 4/2021 |

(Continued)

OTHER PUBLICATIONS

Japanese Office Action mailed Mar. 26, 2024 for Japanese Application No. 2023-006890, a foreign counterpart to U.S. Appl. No. 18/099,062, 17 pages.

(Continued)

*Primary Examiner* — Nelson M Rosario
(74) *Attorney, Agent, or Firm* — Lee & Hayes, P.C.

(57) ABSTRACT

A vision screening device for administering vision screening tests to a patient, to determine the presence of diseases and/or abnormalities in the eye(s) of the patient, is described herein. The vision screening device may include associated methods and systems configured to perform the operations of the vision screening tests. The device may include a radiation source configured to generate near-infrared (NIR) radiation, a sensor configured to capture a grayscale image representing the radiation reflected by the eye(s) of the patient, a white light source, and a camera configured to capture a color image of the eye of the patient. The device may also be configured to generate a composite image based on the grayscale image and/or the color image, determine a difference between a value associated with the eye and an expected value, and generate an output indicative of a condition associated with the eye(s) based on the difference.

16 Claims, 10 Drawing Sheets

(56) References Cited

U.S. PATENT DOCUMENTS

| | | | |
|---|---|---|---|
| 9,427,152 | B2 | 8/2016 | Lewis |
| 9,545,202 | B2 | 1/2017 | Divo et al. |
| 9,931,032 | B2 | 4/2018 | Davis |
| 10,313,608 | B2 | 6/2019 | Nakamure |
| 10,702,147 | B2 | 7/2020 | Lane et al. |
| 11,154,193 | B2 | 10/2021 | Toslak et al. |
| 2007/0171363 | A1 | 7/2007 | Chen |
| 2007/0211212 | A1 | 9/2007 | Bennwik |
| 2009/0079937 | A1 | 3/2009 | Chen et al. |
| 2012/0169995 | A1 | 7/2012 | Mohr et al. |
| 2015/0272438 | A1 | 10/2015 | Ukn |
| 2017/0296049 | A1 | 10/2017 | Uji et al. |
| 2018/0333092 | A1 | 11/2018 | Roshan et al. |
| 2019/0110677 | A1 | 4/2019 | Walsh et al. |
| 2021/0093193 | A1 | 4/2021 | Birkner et al. |
| 2022/0095911 | A1* | 3/2022 | DeAyala ............... G06F 18/214 |
| 2023/0018494 | A1* | 1/2023 | Gribble ............... A61B 3/0008 |

FOREIGN PATENT DOCUMENTS

| | | | |
|---|---|---|---|
| JP | 2012034794 | A | 2/2012 |
| JP | 2013198587 | A | 10/2013 |
| WO | WO2013162471 | A2 | 10/2013 |
| WO | 2019158916 | A1 | 8/2019 |

OTHER PUBLICATIONS

Office Action for Japanese Application No. 2023-006890, Dated Nov. 26, 2024, 8 pages.

The Extended European Search Report and Written Opinion mailed Aug. 3, 2023 for European patent application No. 23152370.5, 8 pages.

Office Action for Chinese Application No. 202310091738.2, Dated Jul. 11, 2025, 22 pages.

Examination Report for European Application No. 23152370.5, dated Mar. 25, 2025, 12 pages.

Office Action for Japanese Application No. 2023-006890, dated Mar. 25, 2025, 6 pages.

Office Action for Chinese Application No. 202310091738.2, dated Dec. 12, 2025, 12 pages.

Wang, et al., "Evaluation of the Efficacy of Laser Photocoagulation", A Chinese Journal of Practical Ophthalmology, Issue 08, Aug. 30, 1997, pp. 460-462.

* cited by examiner

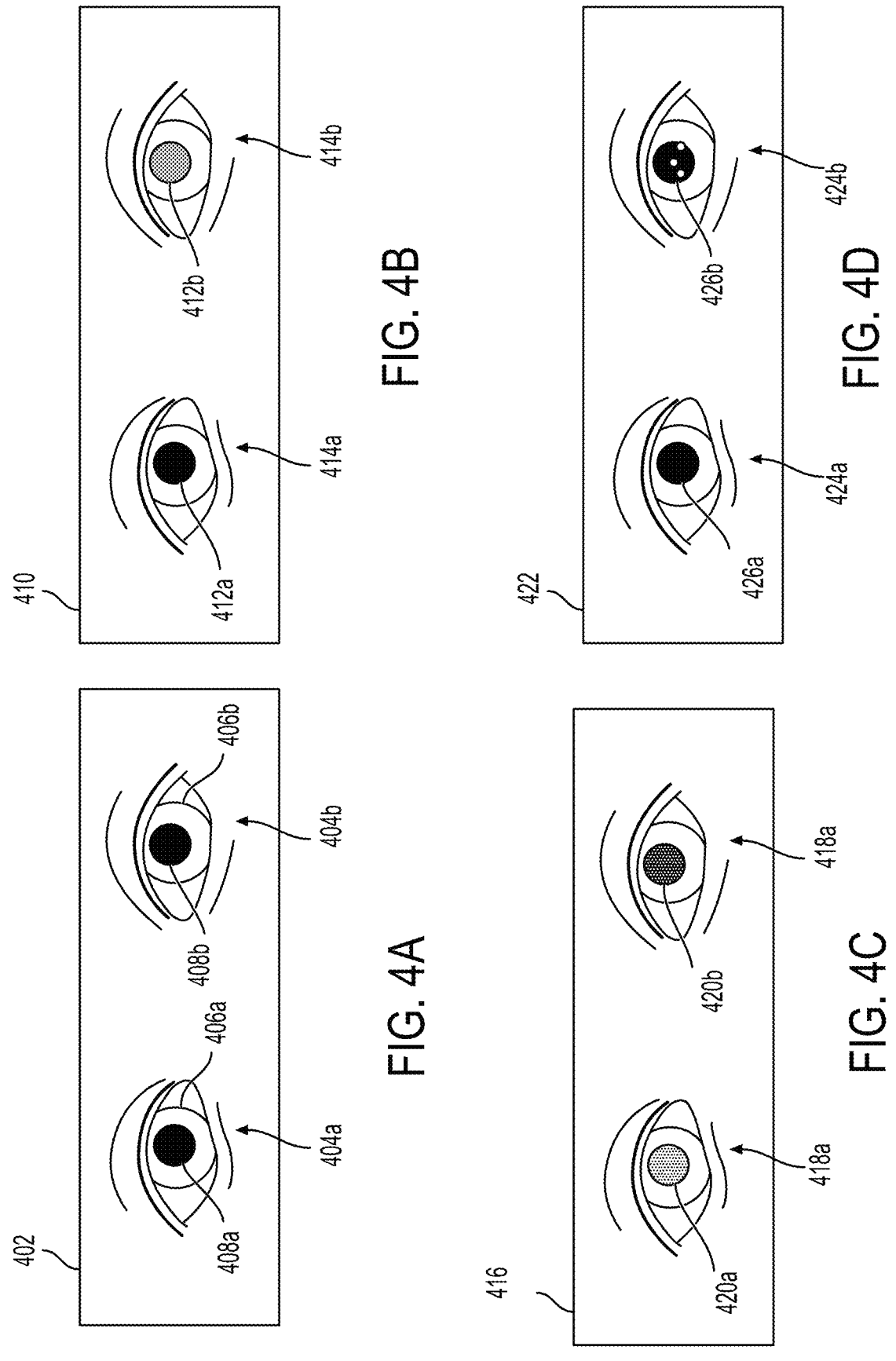

800

SELECT A VISION SCREENING TEST
802

RECEIVE IMAGES OF THE EYE(S)  804
(E.G., COLOR, GRAYSCALE, COMPOSITE, VIDEO)

PERFORM SELECTED VISION SCREENING TEST
806

VISION SCREENING SESSION
COMPLETE?
808

No

YES

GENERATE REPORT
810

VISION SCREENING DEVICE INCLUDING COLOR IMAGING

CROSS-REFERENCE TO RELATED APPLICATIONS

This application is a nonprovisional of, and claims priority to, U.S. Provisional Application No. 63/301,667, filed Jan. 21, 2022, the entire disclosure of which is incorporated herein by reference.

TECHNICAL FIELD

This application is directed to medical equipment. In particular, this application is directed to a vision screening device, and associated systems and methods, for detection and assessment of diseases and disorders of the eye.

BACKGROUND

Vision screening typically includes screening for diseases of the eye. Such screening may include, for example, a transillumination test such as the Bruckner red reflex test. During the red reflex test, the clinician illuminates the eye of the patient with visible light using an ophthalmoscope, and examines the color and other characteristics of the light reflected back by the choroid and the retinal surfaces of the eye. Various diseases and abnormalities of the eyes can be detected using this test, such as corneal or media opacities, cataracts, and retinal abnormalities including tumors and retinoblastoma. Vision screening for diseases is recommended for all age groups. For example, newborns may be screened for congenital eye diseases, while older adults may be screened for the onset of age-related degenerative diseases such as cataracts and retinal diseases. The presence of foreign objects in the eye may also be detected using vision screening under visible light.

In addition, vision screening typically also includes one or more tests to determine various deficiencies associated with the patient's eyes. Such vision tests may include, for example, refractive error tests, accommodation tests, visual acuity tests, color vision screening and the like. Some of the vision screening tests require the use of infrared or near-infrared imaging, while other tests may require imaging under visible light, and/or a display screen to show content to the patient. However, ophthalmic testing devices such as a phoropter, autorefractor and photo-refractors, may only provide the capability to perform a limited range of tests. It would be advantageous to be able to screen for most vision problems and diseases using a single integrated device.

The various examples of the present disclosure are directed toward overcoming one or more of the deficiencies noted above.

SUMMARY

In an example of the present disclosure, a vision screening device includes a radiation source configured to emit radiation of a first wavelength (e.g., in a near-infrared band), a sensor configured to capture radiation reflected by an eye of a patient, a white light source, and a camera configured to capture a color image of the eye of the patient. The vision screening device also includes a processor operably connected to the radiation source, the sensor, the white light source, and the camera, and memory storing instructions executable by the processor. The instructions when executed, cause the processor to cause the radiation source to emit radiation of the first wavelength during a first period of time, cause the sensor to capture a portion of the radiation reflected by the eye of the patient during the first period of time, cause the white light source to illuminate the eye of the patient during a second period of time after the first period of time, and cause the camera to capture a color image of the eye of the patient during the second period of time. The instructions, when executed, also cause the processor to generate a composite image of the eye, wherein the composite image includes a first plurality of pixels representative of a grayscale image indicative of the captured portion of the radiation and a second plurality of pixels representative of the color image, determine a difference between a value associated with the eye and an expected value based on the composite image, and generate an output indicative of a condition associated with the eye based at least in part on the difference.

In another example of the present disclosure, a method includes causing a radiation source to illuminate an eye of a patient during a first period of time, causing a sensor to capture a grayscale image of the eye during the first period of time, causing a white light source to illuminate the eye during a second period of time separate from the first period of time, and causing a camera to capture a color image of the eye during the second period of time. The method also includes generating a composite image of the eye, wherein the composite image derives a first plurality of pixel values from the grayscale image and a second plurality of pixel values from the color image, determining, based on at least one of the color image or the composite image, properties of the eye revealed by NIR and visible light independently based at least in part on this analysis, an output associated with the patient.

In still another example of the present disclosure, a system includes memory, a processor, and computer-executable instructions stored in the memory and executable by the processor. The instructions, when executed, cause the processor to perform operations comprising: causing a radiation source to emit near-infrared (NIR) radiation during a first period of time, causing a sensor to capture a portion of the NIR radiation reflected by an eye of a patient during the first period of time, causing a white light source to illuminate the eye during a second period of time separate from the first period of time, and causing a camera to capture a color image of the eye during the second period of time. The instructions, when executed, also cause the processor to determine, based on the color image and the portion of the NIR radiation, a difference between a value associated with the eye and an expected value, determine that the difference is equal to or greater than a threshold value, and generate, based at least in part on determining that the difference is equal to or greater than the threshold value, an output indicative of a condition of the eye.

BRIEF DESCRIPTION OF THE DRAWINGS

Features of the present disclosure, its nature, and various advantages, may be more apparent upon consideration of the following detailed description, taken in conjunction with the accompanying drawings.

FIGS. 4A-4D illustrate example characteristics that may be used by a vision screening device to determine diseases and abnormalities of an eye from images of the eye, according to examples of the present disclosure.

In the figures, the left-most digit(s) of a reference number identifies the figure in which the reference number first appears. The use of the same reference numbers in different figures indicates similar or identical items or features. The drawings are not to scale.

DETAILED DESCRIPTION

Figure 1:
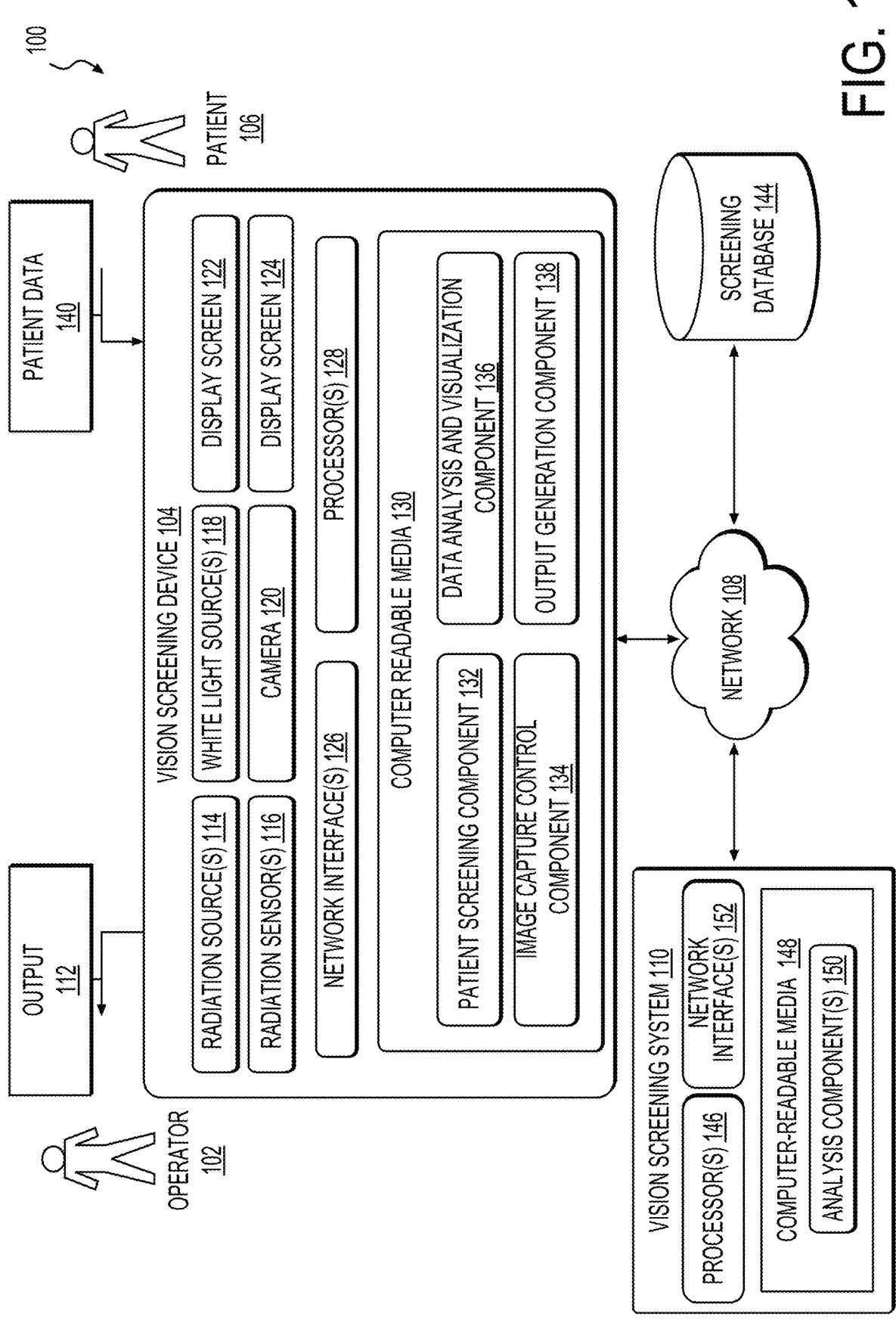
FIG. 1 illustrates an example vision screening device and vision screening system of the present disclosure. In some implementations, components of the example system shown in FIG. 1 may be used to perform one or more screening tests associated with vision screening and/or detection of diseases or abnormalities of the eyes.

The present disclosure is directed to, in part, a vision screening device, and corresponding methods. Such an example vision screening device may be configured to perform one or more vision screening tests on a patient and to output the results of the vision screening test(s) to an operator of the device, such as a clinician or a physician's assistant. Specifically, the present disclosure is directed to devices and methods for screening for diseases and abnormalities of the eye. For example, the vision screening device may capture one or more images of the eye illuminated by radiation of different wavelength ranges of electromagnetic spectrum (e.g., infrared, near-infrared, and visible light). The device may determine, based on analysis of the captured images, one or more diseases and/or abnormalities of the eyes, such as cataracts, tumors, ametropia, foreign body in the eye, corneal abrasions, retinal detachment or lesions, congenital conditions and the like, associated with one or both eyes of the patient.

Based at least in part on the on analysis of the captured images, the device may generate an output including at least one of a recommendation or a diagnosis associated with the patient. Such an output (e.g., the recommendation and/or the diagnosis) may be indicative of diseases or abnormalities detected, indication that the patient requires additional screening, or an indication that the screening was normal (e.g., did not indicate any diseases or abnormalities). For example, the device may determine differences between an image of the left eye and an image of the right eye of the patient, and compare the differences to standard testing data corresponding to normal eyes to provide the recommendation and/or diagnosis. In particular, the standard testing data may provide one or more thresholds or a range of values, and the output generated by the device may be based on the differences being less than the threshold(s) or being within the range of values. The device may also generate visualizations of the captured images for displaying to the clinician or the operator of the vision screening device to assist the clinician or the operator in determining a diagnosis. As such, the methods described herein may provide an automated diagnosis based on the analysis of images captured by the vision screening device. The methods described herein may also provide an automated recommendation based on and/or indicative of such a diagnosis.

As will be described with respect to at least FIG. 1, an example vision screening device associated with screening for diseases and abnormalities of the eyes may include components for capturing images of the eye(s) of the patient under near-infrared as well as visible light radiation. The device may include components for controlling emission of near-infrared and visible light radiation and the corresponding capture of the reflected radiation from the eye(s) during the screening. In examples, near-infrared images may be captured before initiating the capture of visible light images, so that pupils of the eyes(s) of the patient do not constrict, or accommodate, during the screening in response to visible light, and the screening may be completed without the need for dilation of the eyes. The device may further include components for analyzing the captured images to determine disease conditions and/or abnormalities in the eye(s) of the patient, and components for determining and reporting of output(s) indicating the disease conditions and/or abnormalities detected during the screening.

Additional details pertaining to the above-mentioned devices and techniques are described below with reference to FIGS. 1-7. It is to be appreciated that while these figures describe devices and systems that may utilize the claimed methods, the methods, processes, functions, operations, and/or techniques described herein may apply equally to other devices, systems, and the like.

FIG. 1 illustrates an example environment 100 for administering vision screening tests, and in particular, screening tests for detection of diseases and/or abnormalities of eye(s), according to some implementations. As illustrated in FIG. 1, in some examples an operator 102 may administer vision screening tests, via a vision screening device 104, on a patient 106 to determine eye health of the patient 106. As described herein, the vision screening device 104 may perform one or more vision screening tests, including screening for diseases and/or abnormalities of eye(s) when the eyes are illuminated by visible light. In addition, the vision screening device 104 may also be configured to perform other vision screening tests, such as a visual acuity test, a refractive error test, an accommodation test, dynamic eye tracking tests, color vision screening test and/or any other vision screening tests, configured to evaluate and/or diagnose the vision health of the patient 106. In examples, the vision screening device 104 may comprise a portable device configured to perform the one or more vision screening tests. Due to its portable nature, the vision screening device 104 may perform the vision screening tests at any location, from conventional screening environments, such as schools and medical clinics, to physician's offices, hospitals, eye care facilities, and/or other remote and/or mobile locations. It is also envisioned that the vision screening device 104 may be used for administering vision screening tests to all age groups, including newborns and young children and geriatric patients.

As described herein, the vision screening device 104 may be configured to perform one or more vision screening tests on the patient 106. In examples, one or more vision screening tests may include illuminating the eye(s) of the patient 106 with infrared or near-infrared (NIR) radiation, and capturing reflected radiation from the eye(s) of the patient 106. For example, U.S. Pat. No. 9,237,846, the entire disclosure of which is incorporated herein by reference, describes systems and methods for determining refractive error based on photorefraction using pupil images captured under different illumination patterns generated by near-infrared (NIR) radiation sources. In other examples, vision screening tests, such as the red reflex test, may include illuminating the eye(s) of the patient 106 with visible light, and capturing color image(s) of the eye(s) under visible light illumination. The vision screening device 104 may acquire data comprising color images and/or video data of the eye(s) under visible light illumination, and detect pupils, retinas, and/or lenses of the eye(s) of the patient 106. This data may be used to determine differences between left and right eyes, compare the captured images with standard images, or generate visualizations to assist the operator 102 or a clinician in diagnosing diseases and abnormalities of the eye(s) of the patient. The vision screening device 104 may transmit the data, via a network 108, to a vision screening system 110 for analysis to determine an output 112 associated with the patient 106. Alternatively, or in addition, the vision screening device 104 may perform some or all of the analysis locally to determine the output 112. Indeed, in any of the examples described herein, some or all of the disclosed methods may be performed in whole or in part by the vision screening device 104 independently (e.g., without the vision screening system 110 or its components), or by the vision screening system 110 independently (e.g., without the vision screening device 104 or its components). For instance, in some examples, the vision screening device 104 may be configured to perform any of the vision screening tests, and/or other methods described herein without being connected to, or otherwise in communication with, the vision screening system 110 via the network 108. In other example, the vision screening system 110 may include one or more components that are similar to and/or the same as those included in the vision screening device 104, and thus, the vision screening system 110 may be configured to perform any of the vision screening tests, and/or other methods described herein without being connected to, or otherwise in communication with, the vision screening device 104.

As shown schematically in FIG. 1, the vision screening device 104 may include one or more radiation source(s) 114 configured to perform functions associated with administering one or more vision screening tests. The radiation source(s) 114 may comprise individual radiation emitters, such as light-emitting diodes (LEDs), which may be arranged in a pattern to form an LED array. In examples, the radiation source(s) 114 may include near-infrared (NIR) radiation emitters, such as NIR LEDs, for measuring the refractive error of the eye(s) of the patient 106 using photorefraction methods. The NIR radiation emitters of the radiation source(s) 114 may also be used for measuring the gaze angle or gaze direction of the eye(s) of the patient 106. In addition, the radiation source(s) 114 may also include color LEDs for generating color stimuli for display to the patient 106 during a color vision screening test.

The vision screening device 104 may also include one or more radiation sensor(s) 116, such as infrared cameras, configured to capture reflected radiation from the eye(s) of the patient during the vision screening test(s). For example, the vision screening device 104 may emit, via the radiation source(s) 114, one or more beams of radiation, and may be configured to direct such beams at the eye(s) of the patient 106. The vision screening device 104 may then capture, via the radiation sensor(s) 116, corresponding radiation that is reflected back (e.g., from pupils of the eye(s)). In examples, the radiation sensor(s) 116 may comprise NIR radiation sensor(s) to capture reflected NIR radiation while the eye(s) of the patient 106 are illuminated by the NIR radiation source(s) 114. The data captured by the NIR radiation sensor(s) 116 may be used in the measurement of the refractive error and/or gaze angle(s) of the eye(s) of the patient 106. The data may include images and/or video of the pupils, retinas, and/or lenses of the eyes of the patient 106. In some examples, the images and/or video may be in grayscale (e.g., with values between 0 and 128, or between 0 and 256). The data may be captured intermittently, during specific periods of the vision screening test(s), or during the entire duration of the test(s). Additionally, the vision screening device 104 may process the image(s) and/or video data to determine change(s) in the refractive error and/or gaze angle(s) of the eye(s) of the patient 106. The grayscale images of the eye(s) captured under NIR illumination may also be used for screening for diseases and abnormalities of the eye(s) such as ametropia, strabismus, and occlusions.

In examples, the vision screening device 104 may further include visible white light source(s) 118 and camera 120 configured to capture color images and/or video of the eyes under illumination by the white light source(s) 118. The white light source(s) 118 may comprise light-emitting diodes (LEDs) such as an array of LEDs configured to produce white light e.g., a blue LED with a phosphor coating to convert blue light to white light, or a combination of red, blue, and green LEDs configured to produce white light by varying intensities of individual red, blue and green LED activation. Individual LEDs of the array of LEDs may be arranged in a pattern configured to be individually operable to provide illumination from different angles during the vision screening test(s). The white light source(s) 118 may also be configured to produce white light of different intensity levels. The camera 120 may be configured to capture white light reflected from the eyes of the patient to produce digital color images and/or video. The camera 120 may comprise a high-resolution, auto-focus digital camera with custom optics for imaging eyes in clinical applications, as described in further detail with reference to FIG. 2. The color images and/or video captured by the camera 120 may be stored in various formats, such as JPEG, BITMAP, TIFF, etc. (for images) and MP4, MOV, WMV, AVI etc. (for video). In some examples, pixel values in the color images and/or video may be in a RGB (red, green, blue) color space. The color images and/or video of the eye(s) captured under white light illumination may be used for screening for diseases and abnormalities of the eye(s) such as cataracts, media opacities in aqueous and vitreous humors, tumors, retinal cancers and detachment, and the like. In addition, the color images and/or video may be used in conjunction with the grayscale images captured under NIR illumination to generate visualizations to assist in the detection of a wide range of disease conditions of the eye(s).

The vision screening device 104 may also include one or more display screen(s), such as display screen 122 and display screen 124, which may be color LCD (liquid crystal display), or OLED (organic light-emitting diode) display screens. The display screen 122 may be an operator display screen facing a direction towards the operator 102, configured to provide information related to the vision screening tests to the operator 102. In any of the examples described herein, the display screen 122 facing the operator 102 may be configured to display and/or otherwise provide the output 112 generated by the vision screening device 104 and/or generated by the vision screening system 110. The output 112 may include testing parameters, current status and progress of the screening test(s), measurements(s) determined during the test(s), image(s) captured or generated during the screening test(s), a diagnosis determined based on one or more tests, and/or a recommendation associated with the diagnosis. The display screen 122 facing the operator 102 may also display information related to or unique to the patient, and the patient's medical history.

In some examples, the vision screening device 104 may also include a display screen 124 facing in a direction towards the patient 106, and configured to display content to the patient 106. The content may include attention-attracting images and/or video to attract attention of the patient and hold the patient's gaze towards the vision screening device 104. Content corresponding to various vision screening test(s) may also be presented to the patient 106 on the display screen 124. For example, the display screen 124 may display color stimuli to the patient 106 during a color vision screening test, or a Snellen eye chart during a visual acuity screening test. The display screens 122, 124 may be integrated with the vision screening device 104, or may be external to the device, and under computer program control of the device 104.

The vision screening device 104 may transmit the data captured by the radiation sensor(s) 116 and the camera 120, via the network 108, using network interface(s) 126 of the vision screening device 104. In addition, the vision screening device 104 may also similarly transmit other testing data associated with the vision screening test(s) being administered, (e.g., type of test, duration of test, patient identification and the like). The network interface(s) 126 of the vision screening device 104 may be operably connected to one or more processor(s) 128 of the vision screening device 104, and may enable wired and/or wireless communications between the vision screening device 104 and one or more components of the vision screening system 110, as well as with one or more other remote systems and/or other networked devices. For instance, the network interface(s) 126 may include a personal area network component to enable communications over one or more short-range wireless communication channels, and/or a wide area network component to enable communication over a wide area network. In any of the examples described herein, the network interface(s) 126 may enable communication between, for example, the processor(s) 128 of the vision screening device 104, and the vision screening system 110, via the network 108. The network 108 shown in FIG. 1 may be any type of wireless network or other communication network known in the art. Examples of network 108 include the Internet, an intranet, a wide area network (WAN), a local area network (LAN), and a virtual private network (VPN), cellular network connections and connections made using protocols such as 802.11a, b, g, n and/or ac.

The vision screening system 110 may be configured to receive data, from the vision screening device 104 and via the network 108, collected during the administration of the vision screening test(s). In some examples, based at least in part on processing the data, the vision screening system 110 may determine the output 112 associated with the patient 106. For example, the output 112 may include a recommendation and/or diagnosis associated with eye health of the patient 106, based on an analysis of the color image data and/or NIR image data indicative of diseases and/or abnormalities associated with the eye(s) of the patient 106. The vision screening system 110 may communicate the output 112 to the processor(s) 128 of the vision screening device 104 via the network 108. As noted above, in any of the examples described herein one or more such recommendations, diagnoses, or other outputs may be generated, alternatively or additionally, by the vision screening device 104.

As described herein, a processor, such as the processor(s) 128, can be a single processing unit or a number of processing units, and can include single or multiple computing units or multiple processing cores. The processor(s) 128 can be implemented as one or more microprocessors, microcomputers, microcontrollers, digital signal processors, central processing units, state machines, logic circuitries, and/or any devices that manipulate signals based on operational instructions. For example, the processor(s) 128 can be one or more hardware processors and/or logic circuits of any suitable type specifically programmed or configured to execute the algorithms and processes described herein. As shown schematically in FIG. 1, the vision screening device 104 may also include computer-readable media 130 operably connected to the processor(s) 128. The processor(s) 128 can be configured to fetch and execute computer-readable instructions stored in the computer-readable media 130, which can program the processor(s) 128 to perform the functions described herein.

The computer-readable media 130 may include volatile and nonvolatile memory and/or removable and non-removable media implemented in any type of technology for storage of information, such as computer-readable instructions, data structures, program modules, or other data. Such computer-readable media 130 can include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. The computer-readable media 130 can be a type of computer-readable storage media and/or can be a tangible non-transitory media to the extent that when mentioned, non-transitory computer-readable media exclude media such as energy, carrier signals, electromagnetic waves, and signals per se.

The computer-readable media 130 can be used to store any number of functional components that are executable by the processor(s) 128. In examples, these functional components comprise instructions or programs that are executable by the processor(s) 128 and that, when executed, specifically configure the one or more processor(s) 128 to perform actions associated with one or more of the vision screening tests used for the detection and diagnosis of diseases and abnormalities of the eye(s). For example, the computer-readable media 130 may store one or more functional components for administering vision screening tests, such as a patient screening component 132, an image capture control component 134, a data analysis and visualization component 136, and/or an output generation component 138, as illustrated in FIG. 1. At least some of the functional components of the vision screening device 104 will be described in detail below.

In examples, the patient screening component 132 may be configured to store and/or access patient data 140 associated with the patient 106. For example, the patient data 140 may include demographic information such as name, age, ethnicity, and the like. When the vision screening device 104 and/or vision screening system 110 initiates a vision screening test, the patient 106 may provide, or the operator 102 may request, from the patient 106 or a guardian of the patient 106 the patient data 140 regarding the patient's demographic information, medical information, preferences, and the like.

In such examples, the operator 102 may request the data while the screening is in progress, or before the screening has begun. In some examples, the operator 102 may be provided with predetermined categories associated with the patient 106, such as predetermined age ranges (e.g., newborn to six months, six to twelve months, one to five years old, etc.), and may request the patient data 140 in order to select the appropriate category associated with the patient 106. In other examples, the operator 102 may be provided a free form input associated with the patient data 140. In still further examples, an input element may be provided to the patient 106 directly.

Alternatively, or in addition, the vision screening device 104 and/or vision screening system 110 may determine and/or detect the patient data 140 during the vision screening test. For example, the vision screening device 104 may include one or more digital cameras, motion sensors, proximity sensors, or other image capture devices configured to collect images and/or video data of the patient 106, and one or more processors of the vision screening device 104 may analyze the data to determine the patient data 140, such as the age category of the patient 106 or a distance of the patient 106 from the screening device. For example, the vision screening device 104 may be equipped with a range finder, such as an ultra-sonic range finder, an infrared range finder, and/or any other proximity sensor that may be able to determine the distance of the patient 106 from the screening device.

Alternatively, or in addition, the vision screening device 104 may be configured to transmit the images/video data to the vision screening system 110, via the network 108, for analysis to determine the patient data 140. Further, the patient screening component 132 may be configured to receive, access, and/or store the patient data 140 associated with the patient 106 and/or additional patients. For example, the patient screening component 132 may store previous patient information associated with the patient 106 and/or other patients. For instance, the patient screening component 132 may store previous screening history of the patient 106, including data from previous screening such as color images, NIR images, and/or video of the eye(s) of the patient 106. The patient screening component 132 may receive the patient data 140 and/or may access such information via the network 108. For example, the patient screening component 132 may access an external database, such as screening database 144, storing data associated with the patient 106 and/or other patients. The screening database 14 may be configured to store the patient data 140 in association with a patient ID. When the operator 102 and/or the patient 106 enters the patient ID, the patient screening component 132 may access or receive the patient data 140 stored in association with the patient ID of the patient 106.

In examples, the patient screening component 132 may be configured to determine the vision screening test(s) to administer to the patient 106 based at least in part on the patient data 140. For example, the patient screening component 132 may utilize the patient data 140 to determine a testing category that the patient 106 belongs to (e.g., a testing category based on age, medical history, etc.). The patient screening component 132 may determine the vision screening test(s) to administer based on the testing category. For example, if the patient data 140 indicates that the patient is a newborn, the selected vision screening test(s) may include screening for congenital conditions of the eye such as congenital cataracts, retinoblastoma, opacities of the cornea, strabismus and the like. In addition, eye abnormalities may be associated with systemic inherited diseases such as Marfan syndrome and Tay-Sachs disease. For example, a screening test for a characteristic red spot in the eye may indicate Tay-Sachs disease. As another example, if the patient data 140 indicates that the patient is above fifty years old, the patient screening component 132 may determine that the vision screening test(s) include screening for onset of cataracts, macular degeneration and other age-related eye diseases.

The patient screening component 132 may also determine vision screening test(s) based on the patient's medical history. For example, the screening database 144 may store, in the patient data 140, medical history associated with previous vision screening tests of the patient 106, including test results, images of the eye(s), measurements, recommendations, and the like. The patient screening component 132 may access the patient data 140 including medical history from the screening database 144 and determine vision screening test(s) to administer to monitor status and changes in previously detected vision health issues. For example, if a progressive eye disease, such as onset of cataracts or macular degeneration, was detected in a previous screening, further screening may be administered to track the development of the disease. As another example, if the patient 106 had surgery for removal of a tumor of the eye(s), the vision screening test(s) may include screening for further tumors or scarring in the eye(s). The patient screening component 132 may determine a list of vision screening tests to be administered to the patient 106 during a vision screening session, and keep track of the vision screening tests that have already been administered during the vision screening session, as well remaining vision screening tests on the list of vision screening tests to be administered.

In some examples, the computer-readable media 130 may additionally store an image capture control component 134. The image capture control component 134 may be configured to operate the radiation source(s) 114, the radiation sensor(s) 116, the white light source(s) 118, and the camera 120 of the vision screening device 104, so that images of the eye(s) are captured under specific illumination conditions required for each particular vision screening test(s). As discussed, the radiation source(s) 114 may include NIR LEDs for illuminating the eye(s) during capture of grayscale images for measuring the refractive error and/or gaze angle of the eye(s) of the patient 106, and the white light source(s) 118 may include white light LEDs for illuminating the eye(s) during capture of color images of the eye(s) by the camera 120. In examples, the image capture control component 134 may generate commands to operate and control the individual radiation sources, such as LEDs of the NIR LEDs, as well as the LEDs of the white light source 118. Control parameters of the LEDs may include intensity, duration, pattern and cycle time. For example, the commands may selectively activate and deactivate the individual LEDs of the radiation sources 114 and white light sources 118 to produce illumination from different angles as needed by the vision screening test(s) indicated by the patient screening component 132. The image capture control component 134 may activate the NIR LEDs of the radiation source(s) 114 used for measuring the refractive error and/or gaze angle of the eye(s) of the patient 106 in synchronization with the capture of images of the eye(s) by the radiation sensors(s) 116 during the performance of a vision screening test. Similarly, the image capture control component 134 may activate the LEDs of the white light source(s) 118 in synchronization with the capture of color images of the eye(s) by the camera 120.

The individual radiation sources, such as LEDs, of the radiation source(s) 114 or the white light source(s) 118 may be controlled by the image capture control component 134 according to control parameters stored in the computer-readable media 130. For instance, control parameters may include intensity, duration, pattern, cycle time, and so forth, of the NIR LEDs of the radiation source(s) 114 and/or the LEDs producing white light of the white light source(s) 118. For example, the image capture control component 134 may use the control parameters to determine a duration that individual LEDs of the radiation source(s) 114, 118 emit radiation (e.g., 50 milliseconds, 100 milliseconds, 200 milliseconds, etc.). Additionally, the image capture control 134 may utilize the control parameters to alter an intensity and display pattern of NIR LEDs of the radiation source(s) 114 for the determination of refractive error of the eye(s) based on photorefraction and/or gaze angle of the eye(s). With respect to intensity, the image capture control component 134 may control parameters to direct the LEDs of the white light source(s) 118 to emit light at an intensity that is bright enough to capture a color image of the eye(s) using the camera 120, while also limiting brightness to avoid or reduce pupil constriction or accommodation. The image capture control component 134 may also control the intensity of the white light source(s) 118 to gradually increase the intensity at a certain rate while activating the camera 120 to capture images and/or video of the eyes to record response of the pupils of the patient's eyes to the increasing intensity of illumination.

Further, the image capture control component 134 may order the emission of radiation from the source(s) 114, 118 so that the NIR LEDs are activated and the images of the eye(s) under NIR radiation are captured before the activation of the LEDs of the white light source(s) 118. In some examples, this ordering may prevent the constriction of the pupils of the eye(s) in response to white light impinging upon them, and/or may allow for the capture of images of the internal structures of the eye(s) without the need for dilating the pupils of the patient 106. In some examples, the image capture control component 134 may additionally control the radiation source(s) 114,118 to generate patterns such as circular patterns, alternating light patterns, flashing patterns, patterns of shapes such as circles or rectangles, and the like to attract the attention of the patient 106, and/or control color LEDs of the radiation source(s) 114, 118 to display color stimuli such as color dot patterns to the patient 106 during vision screening.

The image capture control component 134 may also control the radiation sensor(s) 116 and the camera 120 to capture images and/or video of the eye(s) of the patient 106 during the administration of the vision screening test(s). For example, the radiation sensor(s) 116 may capture data indicative of reflected radiation from the eye(s) of the patient 106 during the activation of one or more of the radiation source(s) 114. The data may include grayscale image data and/or video data of the eye(s). The image capture control component 134 may synchronize the camera 120 to capture color image(s) and/or video data of the eye(s) with the activation of the white light source(s) 118 so that the eye(s) are illuminated by white light radiation during the capture of the color image and/or video data. In some examples, images of the left and the right eye may be captured under different illumination conditions (e.g., from a different individual source), so that the relative angle of illumination with the optical axis of the particular eye is the same for the left and the right eye. In other examples, images of both eyes may be captured simultaneously under the same illumination. As described herein, the image capture control component 134 of the vision screening device 104 may generate grayscale images of the eye(s) illuminated under NIR radiation, and color images of the eye(s) illuminated under white light. Capturing both the grayscale images and the color images may enable the detection of a wider range of diseases and abnormalities of the eyes.

In some examples, the computer-readable media 130 may also store a data analysis and visualization component 136. The data analysis and visualization component 136 may be configured to analyze the image and/or video data collected, detected, and/or otherwise captured by components of the vision screening device 104 (e.g., by the radiation sensor(s) 116, and the camera 120) during one or more vision screening tests. For example, the data analysis and visualization component 136 may analyze the data to determine location of the pupils of the eye(s) in the images, and identify a portion of the image(s) corresponding to the pupil (e.g., pupil image(s)). The data analysis and visualization component 136 may analyze the pupil image(s) to determine characterizations of appearance of the pupil(s) in the pupil image(s). For example, in the instance of the color image(s) captured by the camera 120, the characterizations may include values corresponding to an average color, variance of color, measure of uniformity, presence of inclusions, and the like. In the instance infrared image(s) captured by the radiation sensor(s) 116, the characterizations may include average grayscale value and variance of grayscale values, instead of the color, in addition to measures of uniformity and the presence of inclusions. The data analysis and visualization component 136 may further compare the left pupil image(s) and the right pupil image(s) to determine differences in appearance between the left and right pupils. For example, the differences may correspond to a difference in average color value, average grayscale value, or uniformity between the left pupil image(s) and right pupil image(s). In normal eyes, an expected value of a characteristic (e.g., average color value, grayscale value, measure of uniformity, etc.) associated with one pupil image may be approximately same as a value of the characteristic in the other pupil image. The data analysis and visualization component 132 may also compare the pupil image(s) with standard pupil image(s) and/or pupil image(s) of the patient 106 captured during previous vision screening(s) to determine differences in appearance, such as differences in average color value or grayscale value, differences in the measure of uniformity, differences in detected inclusions, and the like. In such examples, an expected value of a characteristic of the pupil image(s) may correspond to the value of the characteristic in the standard pupil image(s) or previously-captured pupil image(s) of the patient 106. In any of the examples above, all captured image(s) or a subset of the captured grayscale and/or color images may be used to determine differences. In some examples, grayscale image(s) may not be used, and the difference may be determined based on the color image(s). It is to be noted that pixels of grayscale images may also be considered to have a color value, wherein the color value is determined by using the same grayscale value for each of the three color channels (e.g., RGB). For example, a pixel with a grayscale value of 128, may be determined to have a color value of (128, 128, 128) in the RGB color space. The data analysis and visualization component 136 may also apply additional image processing steps to the grayscale image(s) and/or the color image(s) which may improve detection of disease states. For example, images may be sharpened, specific colors may be boosted or attenuated, color or brightness of the images may be balanced, and the like. Additional details pertaining to the above-mentioned data analysis to determine differences are described below with reference to FIG. 4.

Further, the data analysis and visualization component 136 may be configured to receive, access, and/or analyze standard data associated with vision screening. For example, the data analysis and visualization component 136 may be configured to access or receive data from one or more additional databases (e.g., the screening database 144, a third-party database, etc.) storing testing data, measurements, and/or values indicating various thresholds or ranges within which measured values should lie. Such thresholds or ranges may be associated with patients having normal vision health, and may be learned or otherwise determined from standard testing. The data analysis component and visualization component 136 may utilize the standard data for comparison with the average values and differences determined during the vision screening test(s) as described above. For example, the standard data may indicate a threshold or a range for a difference between color values of the left and right pupil images, where a difference greater than the threshold, or outside the range, corresponds to an abnormality in the eye(s) of the patient. Alternatively or in addition, the data analysis and visualization component 136 may access a previous vision screening of the patient 106 and compare the values and differences with corresponding data from the previous screening(s). For example, an average color value of the pupil may be compared with an average color value from a previous screening to determine a difference. This difference may then be compared with standard thresholds or ranges to determine presence of an abnormality, as described above. Separate threshold(s) and/or range(s) may be indicated in the standard data for different types of diseases and abnormalities. In addition, the threshold(s) and/or range(s) associated with the vision screening test may also be based on the testing category of the patient 106 (e.g., the age group or medical history of the patient 106), where the threshold(s) and/or range(s) may be different for different testing categories. The data analysis and visualization component 136 may store as a part of the patient data 140, images and/or video captured or generated during the vision screening test(s), measurements associated with the vision screening test(s), test results, and other data in a database (e.g., in the screening database 144) for comparison of data over time to monitor vision health status and changes in vision health. In some examples, the stored images may include images of the face or partial face (e.g., eyes and part of nose) of the patient 106.

Based on the comparison with a threshold and/or range described above, the data analysis and visualization component 136 may generate a normal/abnormal or a pass/refer determination for each of the eyes of the patient 106. For example, if all values and differences measured are less than on equal to corresponding threshold(s), or fall within the corresponding range(s) of the standard data, a "normal" or "pass" determination may be made by the data analysis and visualization component 136, and an "abnormal" or "refer" determination made otherwise to indicate a referral for further screening. Alternatively, or in addition, the data analysis and visualization component 136 may generate a normal/abnormal determination for each of the diseases and/or abnormalities screened for during the vision screening session.

In examples, the data analysis and visualization component 136 may utilize one or more machine learning techniques to generate a diagnosis of specific diseases and/or types of abnormalities. For example, machine learning (ML)

models may be trained with normal images of eyes, and images of eyes labeled as exhibiting various disease conditions and abnormalities. The trained ML model(s) may then generate an output indicating a disease or abnormality diagnosis when provided, as input, an image of the eye captured during the vision screening of the patient 106. In such examples, the data analysis and visualization component 136 may directly generate the output by providing an image of the eye as input to the trained ML model(s), without computing differences between pupil images or applying comparisons with a threshold and/or range. In some examples, a plurality of trained ML model(s) may be used, each ML model being trained to detect a specific disease or abnormality. In such examples, each ML model outputs a binary present/absent indication to indicate if the input image exhibits the disease or abnormality that the ML model is trained to detect. The data analysis and visualization component 136 may provide an image of the eye as input to each ML model of the plurality of trained ML model(s) for detecting one or more of a plurality of diseases and abnormalities. In examples, the ML models may be neural networks, including convolutional neural networks (CNNs). In other examples, the ML models can also include regression algorithms, decision tree algorithms, Bayesian classification algorithms, clustering algorithms, support vector machines (SVMs) and the like.

The data analysis and visualization component 136 may also generate visualizations of the eye(s) using the image(s) and/or video data captured by the radiation sensor(s) 116 and/or the camera 120. For example, a first visualization may include a composite image of the eye(s) incorporating both color information from the color image(s) and grayscale information from the grayscale image(s) captured by the radiation sensor(s) 116 under NIR illumination. The generation of the first visualization may include detection and identification of structures of the eye(s) such as pupils and/or lenses, followed by registration of the grayscale image(s) and the color image(s) so that the pupils are located in the same position in both types of image(s). The composite image may then be generated by using grayscale pixel values from the grayscale image(s) in some portions of the composite image and color pixel values from the color image(s) in other portions of the composite image. The portions of the composite image using grayscale pixel values and the portions using color pixel values may correspond to areas depicting different structures of the eye(s) (e.g., fovea, retina, cornea etc.). The composite image may more clearly delineate structures of the eye(s) for improved detection and assessment of diseases and/or abnormalities of the eye(s).

In another example, a second visualization may include a sequence of still images, or an animated video comprising the sequence of still images. In some instances, the sequence of images may be captured by the radiation sensor(s) 116 or the camera 120 while the eye(s) are illuminated by the radiation source(s) 114 or white light source(s) 118 at a progression of different angles along different axes with respect to the optical axis, including an angle of approximately zero degrees relative to the optical axis. For instance, in some examples, the radiation emitted by the radiation source(s) 114 or white light source(s) 118 may be emitted substantially parallel to and/or substantially along the optical axis. In such examples, the emitted radiation may be coaxial or near-coaxial with the optical axis. In some examples, the visualization may include graphics and/or color-coding indicative of areas of the image of the eye(s) that are flagged as being abnormal. Further examples of visualizations, including additional details pertaining to the first and second visualization, are described below with reference to FIGS. 5A and 5B. As described herein, the data analysis and visualization component 136 of the vision screening device 104 may process the grayscale images and the color images of the eye(s) captured during the administration of the vision screening test(s), to determine diseases and/or abnormalities associated with the eye(s) of the patient. In addition, the data analysis and visualization component 136 may generate, based on the grayscale and color images, visualizations of the eye(s) that aid a clinician or an operator of the vision screening device 104 to identify diseases and/or abnormalities of the eye(s).

The computer-readable media 130 may additionally store an output generation component 138. The output generation component 138 may be configured to receive, access, and/or analyze data from the data analysis and visualization component 136, and generate the output 112. For example, the output generation component 138 may utilize the normal/ abnormal determinations of the data analysis and visualization component 136 to generate a recommendation in the output 112. The recommendation may indicate whether the screening results of the patient 106 indicate normal eye health, or further screening is needed based on one or more of the screening tests resulting in an "abnormal" finding. In addition, the output generation component 138 may incorporate all or a subset of the visualizations generated by the data analysis and visualization component 136 into the output 112 for aiding in diagnosis of the condition of the eye(s). Portions of the images and/or video captured by the radiation sensor(s) 116 or the camera 120 may also be included in the output 112. Additionally, if abnormality is determined, the output generation component 138 may incorporate a likely diagnosis into the output 112 based on the analysis by the data analysis and visualization component 136. The output 112 may be presented to the operator of the device via an interface of the device (e.g., on the display screen 122 of the vision screening device 104). In examples, the operator display screen may not visible to the patient, e.g., the operator display screen may be facing in a direction opposite the patient. The output generation component 138 may also store the output 112, which may include a recommendation, diagnosis, measurements, captured images/video and/or the generated visualizations in a database, such as the screening database 144, for evaluation by a clinician, or for access during subsequent vision screening(s) of the patient 106. The screening database 144 may provide access to authorized medical professionals to enable printing of reports or further assessment of the data related to the screening of the patient 106.

Although FIG. 1 illustrates example processor(s) 128 and computer-readable media 130 storing a patient screening component 132, an image capture control component 134, a data analysis and visualization component 136, an output generation component 138 and/or other components and/or other items as components of the vision screening device 104, in any of the examples described herein, the vision screening system 110 may include similar components and/ or the same components. In such examples, the vision screening system 110 may include processor(s) 146 and computer-readable memory 148 that are configured to perform the functions of some or all of the components in the computer-readable memory 130 of the vision screening device 104. For example, one or more of the components in the computer-readable memory 130 may be included in analysis component(s) 150 of computer-readable memory 148 and be executable by the processor(s) 146. In such examples, the vision screening system 110 may communicate with the vision screening device 104 using network interface(s) 152, and via the network 108, to receive data from the vision screening device 104 and send results (e.g., output 112), back to the vision screening device 104. The vision screening system 110 may be implemented on a computer proximate the vision screening device 104, or may be at a remote location. For example, the vision screening system 110 may be implemented as a cloud service on a remote cloud server.

The network interface(s) 152 may enable wired and/or wireless communications between the components and/or devices shown in system 100 and/or with one or more other remote systems, as well as other networked devices. For instance, at least some of the network interface(s) 152 may include a personal area network component to enable communications over one or more short-range wireless communication channels. Furthermore, at least some of the network interface(s) 152 may include a wide area network component to enable communication over a wide area network. Such network interface(s) 152 may enable, for example, communication between the vision screening system 110 and the vision screening device 104 and/or other components of the system 100, via the network 108. For instance, the network interface(s) 152 may be configured to connect to external databases (e.g., the screening database 144) to receive, access, and/or send screening data using wireless connections. Wireless connections can include cellular network connections and connections made using protocols such as 802.11a, b, g, and/or ac. In other examples, a wireless connection can be accomplished directly between the vision screening device 104 and an external system using one or more wireless protocols, such as Bluetooth, Wi-Fi Direct, radio-frequency identification (RFID), infrared signals, and/or Zigbee. Other configurations are possible. The communication of data to an external database can enable report printing or further assessment of the patient's visual test data. For example, data collected and corresponding test results may be wirelessly transmitted and stored in a remote database accessible by authorized medical professionals.

It should be understood that, while FIG. 1 depicts the system 100 as including a single vision screening system 110, in additional examples, the system 100 may include any number of local or remote vision screening systems substantially similar to the vision screening system 110, and configured to operate independently and/or in combination, and configured to communicate via the network 108.

As discussed herein, FIG. 1 depicts an exemplary vision screening device 104 that includes components for administering vision screening tests to a patient. In some examples, one or more components may be implemented on a remote vision screening system 110 communicating with the vision screening device 104 over a network 108. The vision screening device 104 and its components are described in detail with reference to the remaining figures.

Figure 2:
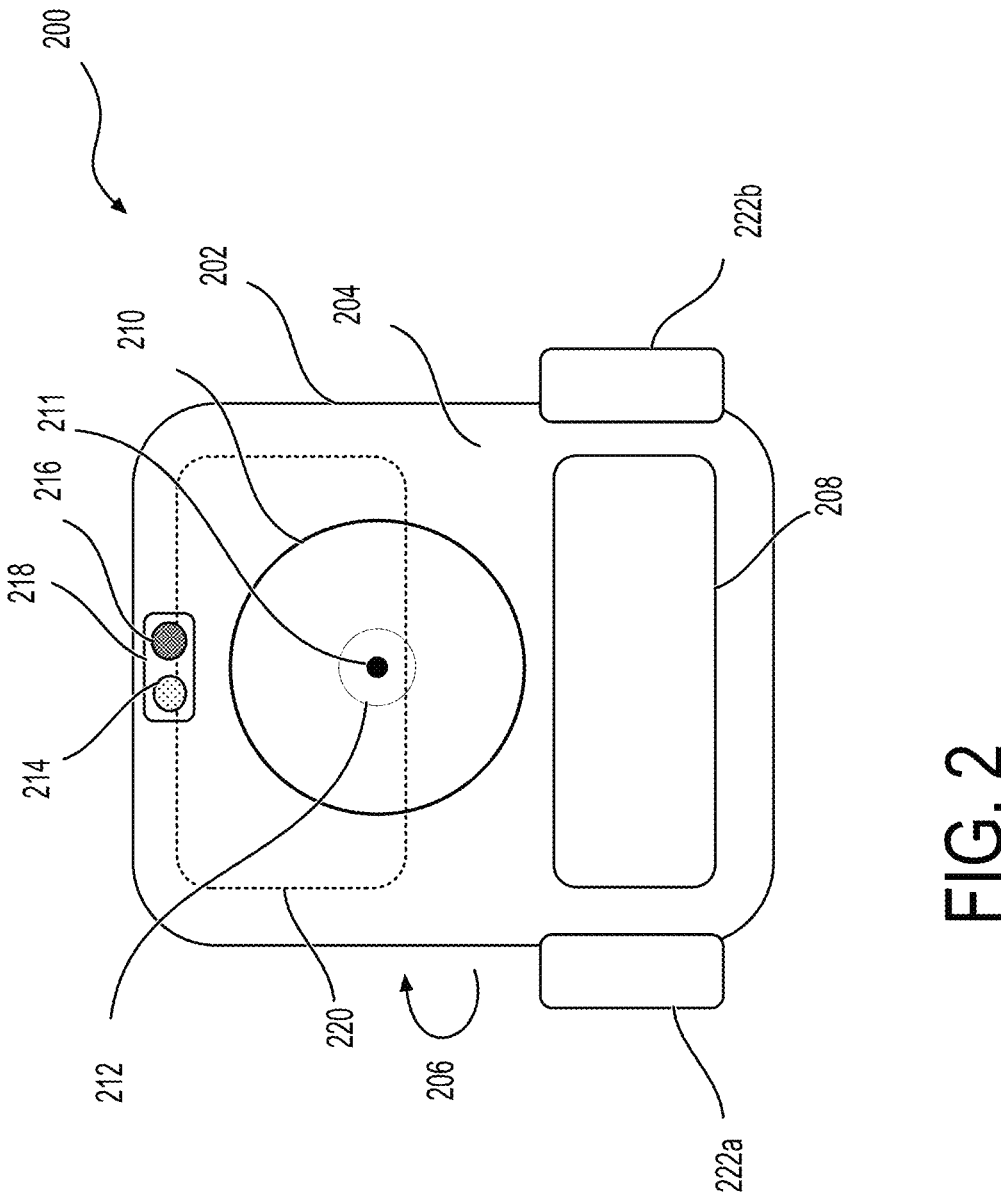
FIG. 2 illustrates an example vision screening device of the present disclosure.

FIG. 2 illustrates an embodiment of a vision screening device 200 according to some implementations. The example vision screening device 200 may include one or more of the same components included in the vision screening device 104 of the system 100. In some additional examples, the vision screening device 200 can include different components that provide similar functions to the vision screening device 104.

The vision screening device 200 may be a tablet-like device, which may include one or more processors, computer-readable media, and network interface(s) associated therewith (not shown) in a housing 202. The housing 202 may include a front surface 204 configured to face a patient (such as the patient 106) during use of the vision screening device 200, and a back surface 206, opposite the front surface 204, configured to face an operator of the vision screening device 200 (such as the operator 102) during use of the vision screening device 200. The front surface 204 may include a display screen 208, which may be substantially similar to or the same as the display screen 124, radiation source(s) 210, which may be substantially similar to or the same as the radiation source(s) 114, radiation sensor(s) 212, which may be substantially similar to or the same as the radiation sensor(s) 116, white light source(s) 214, which may be substantially similar to or the same as the white light source(s) 118, and/or a camera 216, which may be substantially similar to or the same as the camera 120.

The radiation source(s) 210 may be configured to emit radiation in the infrared band and/or the near-infrared (NIR) band. For instance, the radiation source(s) 210 may comprise an arrangement of NIR LEDs configured to determine refractive error associated with one or more eyes of the patient. The NIR LEDs of the radiation source(s) 210 may be disposed radially around a central axis 211 of the vision screening device 200, with the radiation sensor(s) 212 being disposed substantially along the central axis 211. The NIR LEDs may be used to provide eccentric illumination of the eye(s) of the patient during the vision screening test(s) by aligning the central axis 211 with an optical axis of the eye(s) (e.g., for measuring refractive error using photorefraction techniques). The arrangement of NIR LEDs will be described in further detail with reference to FIG. 3B.

The vision screening device 200 may also include a white light source 214, and a visible light camera 216 configured to captured color images and/or video of the eyes of the patient. In some examples, the white light source 214 and the camera 216 may be included in an image capture module 218. The camera 216 of the image capture module 218 may include a high-resolution lens with a narrow field of view suitable for imaging eyes in a vision screening setting. Such a lens may incorporate folded prism slim lens technology which allows for telephoto zoom while maintaining a low height profile. The optical system used in folded prism lenses bends and focuses light while it is reflected back and forth inside optical prisms, reducing the thickness of the lens and allowing for a substantially low-height form factor. As discussed above with reference to FIG. 1, some vision screening tests may require color images of pupils and/or lenses of the eyes of the patient to determine the presence of diseases and/or abnormalities. In some examples, the camera 216 may be equipped with a high-resolution zoom capability to enable the capture of close-up images of the eyes of the patient from which the pupils and/or lenses of the eyes can be localized. In other examples, the camera 216 may use a fixed focal length lens with placement of the eyes being adjusted to achieve an in-focus image. The white light source 214, which is more commonly referred to as a flash, may include one or more visible light LEDs of adjustable intensity. The intensity level of the white light source 214 may be controlled by the one or more processors of the vision screening device 200. The one or more processors of the vision screening device 200 may also synchronize timing of activation of the white light source(s) 214 with the capture of an image by the camera 216.

The vision screening device 200 may also include a display screen 220 disposed on the back surface 206 of the housing 202 that substantially faces the operator (e.g., the operator 102), during operation of the vision screening device 200. The display screen 220, which may be touch-sensitive to receive inputs from the operator, may display a graphical user interface configured to display information to the operator and/or receive input from the operator during a vision screening test. For example, the display screen 220 may be used by the operator to enter information regarding the patient, or the vision screening test(s) being administered. Further, the display screen 220 may be configured to display information to the operator regarding the vision screening test being administered (e.g., parameter settings, progress of screening, options for transmitting data from the vision screening device 200, one or more measurements, and/or images or visualizations generated during the vision screening, etc.). The display screens 208, 220 may comprise, for example, a liquid crystal display (LCD) or active matrix organic light emitting display (AMOLED).

In some examples, the vision screening device 200 may include hand grips 222a and 222b for holding the vision screening device 200 with stability during the vision screening tests. As discussed herein, FIG. 2 depicts an exemplary vision screening device 200 that includes components for administering one or more vision screening test(s) to a patient. The vision screening device 200 is intended to perform an entire vision screening which may include multiple, different vision screening tests including screening for multiple diseases, abnormalities and conditions of the eyes of the patient. The vision screening device 200, as shown, has the additional features of being light weight enough to be hand-held, by using the hand grips 222a and 222b for the right and left hand of the operator respectively as an example, allowing for portability and ease-of-use in patients as young as newborn. The vision screening device 200 provides the radiation sources and image capture sensors needed for NIR imaging, as well as color imaging under white light illumination as required for one or more vision screening test(s), in a compact and substantially planar arrangement, enabling the light weight and portable form factor of the vision screening device 200.

Figure 3A:
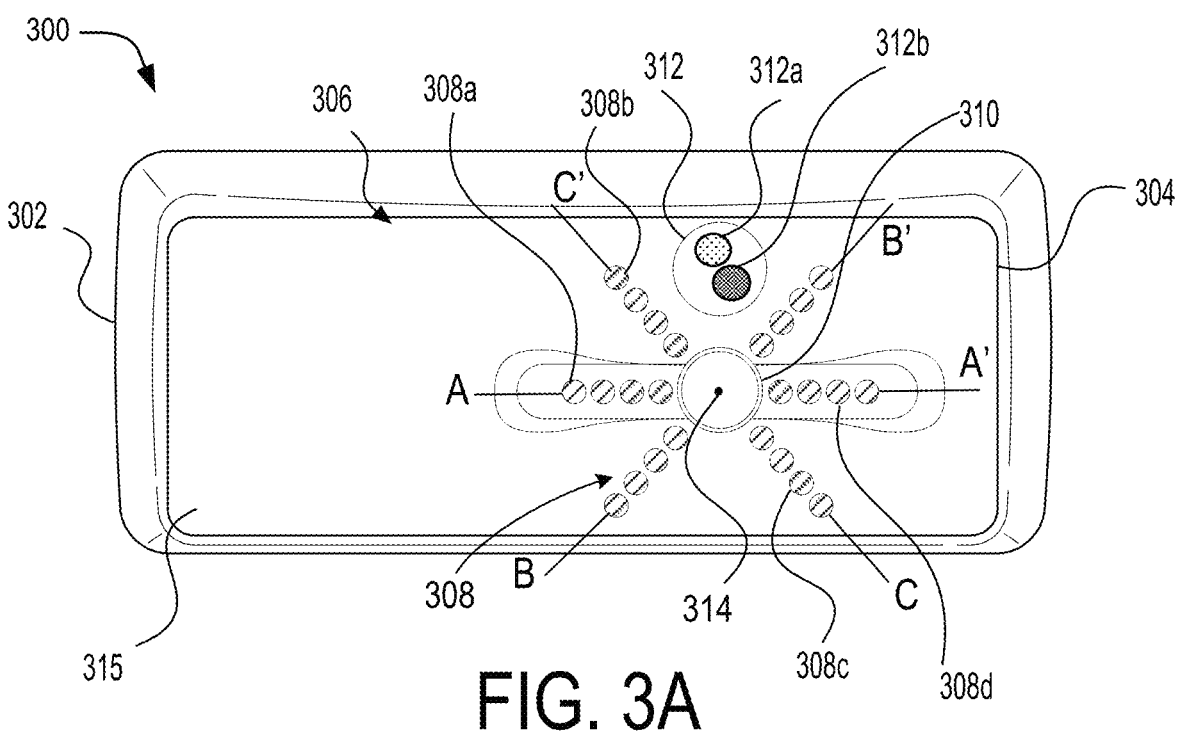
FIG. 3A illustrates another example vision screening device of the present disclosure.

FIG. 3A illustrates another embodiment of a vision screening device 300 according to some implementations. The example vision screening device 300 may include one or more of the same components included in the vision screening devices 104, 200. In some additional examples, the vision screening device 300 can include different components that provide similar functions to the vision screening devices 104, 200.

In the example shown, the vision screening device 300 includes a housing 302 with a transparent display screen 304, such as a transparent organic light emitting display (OLED), facing a first end 306 of the vision screening device 300, the first end 306 facing a patient (e.g., the patient 106). The display screen 304 may cover optical components of the vision screening device 300, such as an array 308 of LEDs acting as radiation source(s), which may be substantially similar to or the same as the radiation source(s) 114, radiation sensor(s) 310, which may be substantially similar to or the same as the radiation sensor(s) 116, and an image capture module 312 comprising a white light source 312a and a digital camera 312b, which may be substantially similar to or the same as the white light source(s) 118 and the camera 120. Though the white light source 312a is shown proximate the digital camera 312b, in some examples, the white light source 312a and/or additional white light source(s) may be disposed at other locations on the housing 302 (e.g., the white light source 312a and/or additional white light source(s) may be disposed at one or more corner(s) 315 of the housing 302, along or proximate one or more sides or edges of the housing 302, and/or at any other location). Since the display screen 304 is transparent, radiation from the radiation sources(s) 308 and/or white light from the white light source 312*a* of the image capture module 312 may reach the patient's eye(s), and reflected radiation from the patient's eye(s) may be received by the radiation sensor(s) 310 and/or the camera 312*b* of the image capture module 312 by traveling through the display screen 304 without attenuation and change in direction. The array 308 may be comprised of individual NIR LEDs (e.g., NIR LEDs 308*a*, 308*b*, 308*c*, 308*d*), distributed in a pattern around the radiation sensor(s) 310, as shown. As also shown, the NIR LEDs 308*a*-308*d* may be arranged along different axes, such as axis A-A', B-B' and C-C', which will be described in further detail with reference to FIG. 3B. The radiation sensor(s) 310 is located substantially along a central axis 314 of the vision screening device 300, similar to the central axis 211 of the vision screening device 200. Though the individual NIR LEDs of array 308 are shown as radiating outwards from the centrally located radiation sensor(s) 310, other patterns of placement of the NIR LEDs of the array 308 with more or fewer individual NIR LEDs are also envisioned. As described with reference to FIG. 2, the arrangement of NIR LEDs of the array 308 described herein may provide eccentric illumination required for measuring refractive error using photorefraction techniques.

Figure 3B:
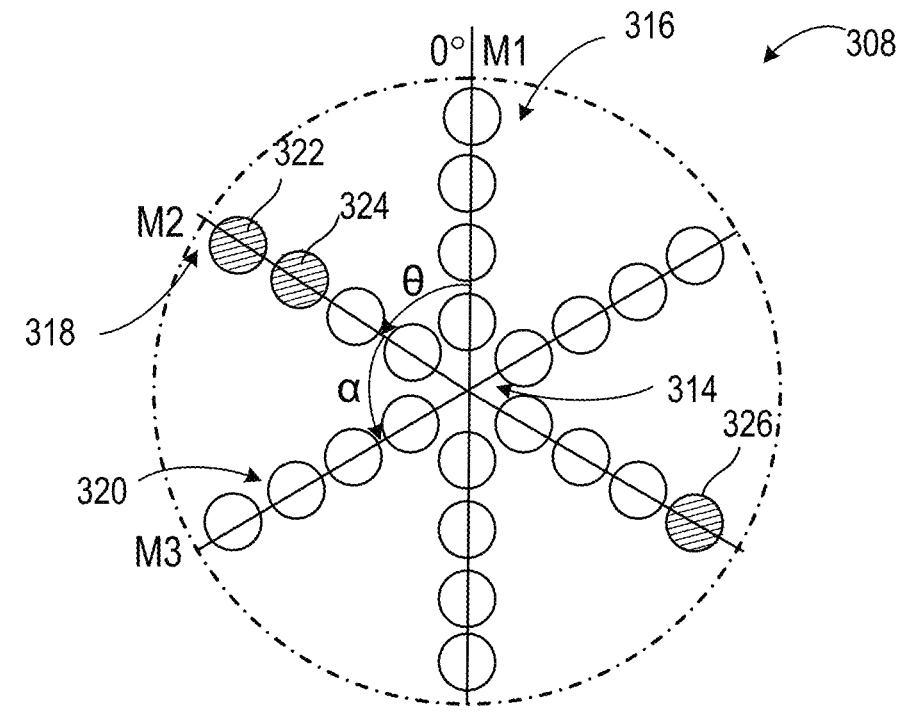
FIG. 3B illustrates an arrangement of radiation sources of an example vision screening device of the present disclosure.

FIG. 3B illustrates an expanded view of the array 308 of NIR LEDs. In examples, the array 308 may include more or fewer individual LEDs than those shown in the example. The example arrangement of individual NIR LEDs of array 308 shown in FIG. 3B includes a row 316 of NIR LEDs that extend generally coaxially across the array 308 along a first axis M1 of the array 308, which may correspond to the axis A-A' of FIG. 3A. The array 308 may also include a row 318 along a second axis M2, which may correspond to axis B-B' of FIG. 3A, at an angle of θ relative to the row 316, and a row 320 along a third axis M3, which may correspond to axis C-C', at an angle of α relative to the row 318, as shown. The angles θ and α may be any acute angle (e.g., 60°). In examples, the axis M1 may also be referred to as a first meridian of the array 308, the axis M2 as a second meridian of the array 308, and the axis M3 as a third meridian of the array 308, and the three axes M1, M2, M3 may intersect at the central axis 314 of the vision screening device 300. In some examples, additional LEDs may be located along one or more axes M1, M2, M3 spaced away from the array 308.

The individual LEDs of the array 308 may be activated in a sequence (e.g., by the image capture control component 134) to generate illumination at different angles or eccentricities, as will be described in further detail with reference to FIG. 3C. For example, LED 322 may be activated first, followed by the LED 324, adjacent to the LED 322, and so on to LED 326 in a sequence progressively along the axis M2. The activation sequence may move through the individual LEDs along the first axis M1, followed by the second axis M2, and the third axis M3. Additionally, the LEDs 322 and 324 may also be activated substantially simultaneously in order to simulate a source location of the combined radiation using a diffuser (not shown). In such examples, an amount of current applied to the LED 322 and the LED 324 may be further controlled (e.g., by the image capture control component 134) to achieve a desired simulated source location of the combined radiation, allowing for generation of illumination at additional angles or eccentricities without having to mechanically move the array 308.

Figure 3C:
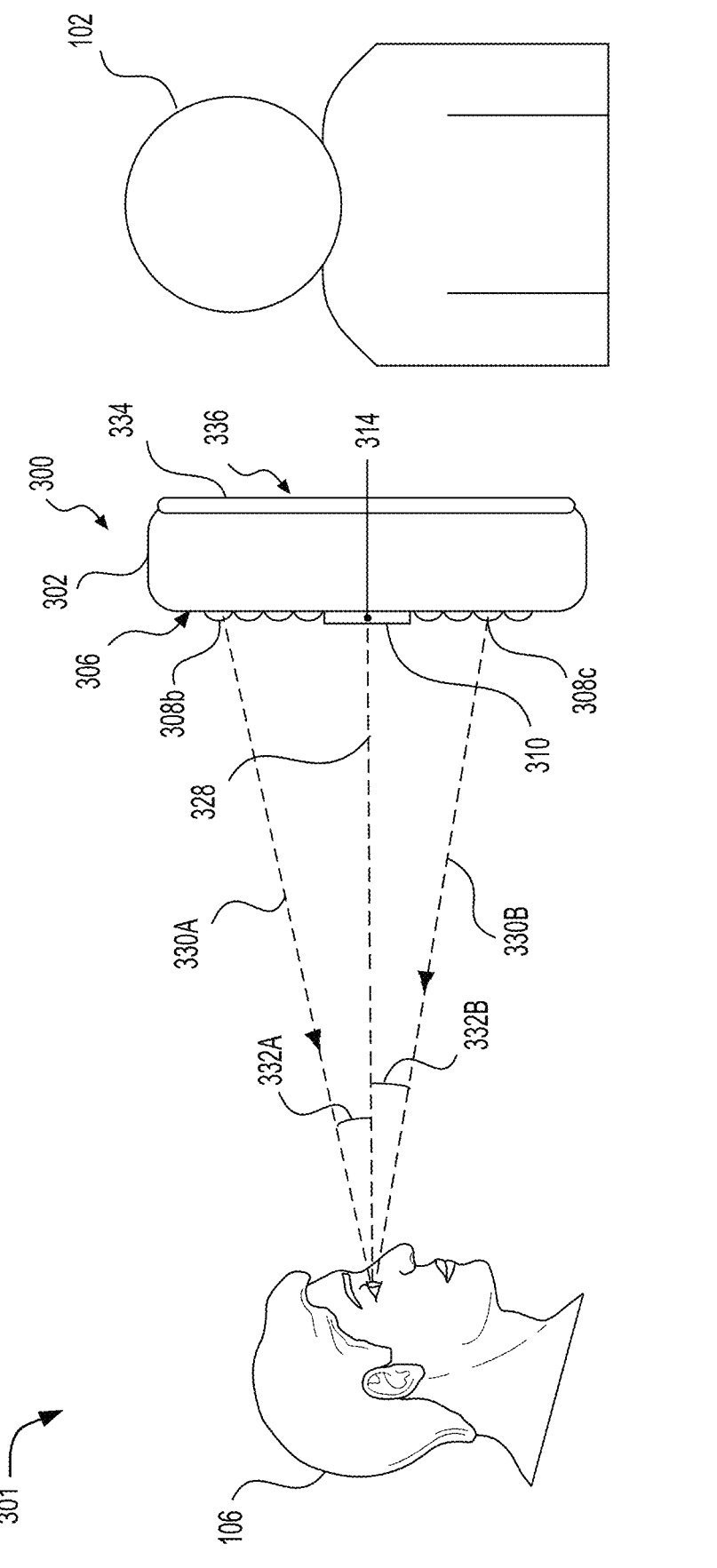
FIG. 3C provides a schematic illustration of an example vision screening system of the present disclosure.

FIG. 3C is a schematic illustration of an example vision screening system 301 using the vision screening device 300 to administer vision screening test(s) to the patient 106 by the operator 102, according to examples of the present disclosure. In examples, the central axis 314 of the vision screening device 300 may be substantially aligned or collinear with an optical axis 328 of the patient's eye(s), as shown. As discussed above with reference to FIG. 1, the image capture control component 134 of the vision screening device may control the individual radiation sources, such as LEDs 308*a*-308*d* or 322, 324 of the array 308, to emit radiation. The radiation emitted by the individual LEDs may impinge on the eye(s) of the patient 106 at different angles relative to the optical axis 328. For example, radiation beam 330A emitted by the LED 308*b* may subtend an angle 332A with the optical axis 328, while radiation beam 330B emitted by the LED 308*c* may subtend an angle 332B, different from angle 332A. Therefore, activation of LEDs of the array 308, individually or in groups, may be used to generate radiation impinging on the eye(s) of the patient 106 at different angles. In some examples, the angles 332A, 332B may be approximately zero degrees relative to, for example, the optical axis 328 (e.g., the illumination may be coaxial or near-coaxial with the central axis 314). For each angle of illumination, reflected radiation from the eye(s) of the patient 106 traveling along the optical axis 328 may be captured by the radiation sensor(s) 310 located along the central axis 314 which is aligned with the optical axis 328, to generate images of the eye(s) under illumination from each angle relative to the optical axis 328. Though described herein with reference to array 308 of NIR LEDs, illumination from different angles with respect to the optical axis 328 may also be generated by the white light source(s) 118, 214, 312*a* using an array or series of individual white light LEDs arranged in a two-dimensional array or a linear pattern, similar to the NIR LEDs of the array 308 described above, as described further with reference to FIG. 3D below.

The vision screening device 300 may also include an additional display screen 334 disposed on the housing 302 of the vision screening device 300 on a side 336 opposite the front side 306. The display screen 334 may face the operator 102, and be configured to provide information related to the vision screening test(s) to the operator 102, similar to display screen 122 described with reference to FIG. 1. In some examples, the display screen 334 may be separate from (e.g., not attached to the housing 302) the vision screening device 300, but operably coupled with and under control of the vision screening device 300.

Figure 3D:
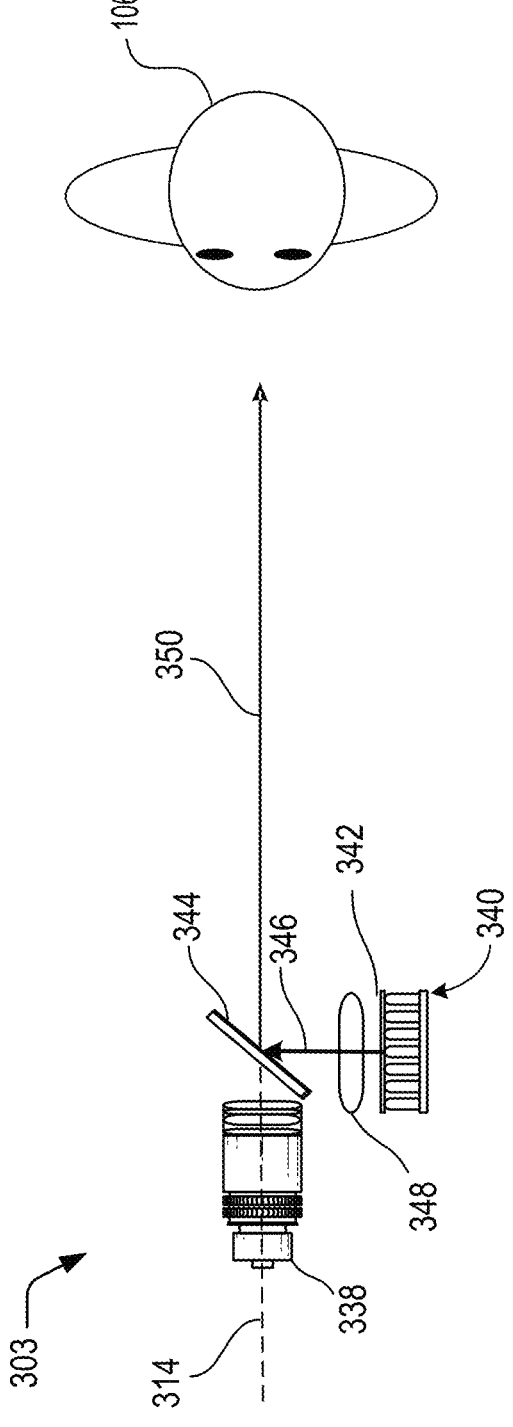
FIG. 3D provides another schematic illustration of the example vision screening device of the present disclosure.

FIG. 3D illustrates an example system 303 including components of the vision screening system 301 according to examples of the present disclosure. The example system 303 illustrates a camera 338, a white light LED array 340 including the white light source(s) 118, a diffuser 342, and a partial reflector 344. Other components of the vision screening system 301 have been omitted in the example system 303 for clarity, however it is understood that any of the components of, for example, the vision screening device 300 or of the vision screening system 301 described above may be included in the example system 303 shown in FIG. 3D.

In examples, radiation 346 (e.g., light) emitted by one or more LEDs of the LED array 340 passes through the diffuser 342 and impinges on the partial reflector 344. In examples, the partial reflector 344 may be a beam splitter, an arrangement of mirrors, a prism, or any other optical component configured to reflect a first portion of the radiation impinging on it while transmitting a second portion of the radiation. In some examples, the partial reflector 344 is placed at an angle of approximately 45 degrees with respect to the central axis 314 of the vision screening system 301, 303 which may be substantially aligned or coaxial with an optical axis of the eye(s) of a patient 106, as discussed with reference to FIG. 3C. As shown, the central axis 314 may also be substantially aligned or coaxial with a lens of the camera 338. The diffuser 342 may act as a blur smoothing filter for the radiation 346 emitted by the LEDs in the LED array 340. In some examples, a lens 348 may be configured to focus the radiation 346 emitted by the LED array 340 to impinge on the partial reflector 344. However, one or more additional optical components may be included to modify the radiation 346 reaching the partial reflection 344. In the example shown in FIG. 3D, at least a portion 350 of the radiation 346 may reflect off of the partial reflector 344, and may be directed to one or both eyes of the patient 106. While the portion 350 of the radiation 346 is directed at the eye(s) of the patient 106, the camera 338 may capture one or more images and/or video of the eye(s) of the patient 106. In examples, the image(s) and/or video may depict radiation that is reflected by the pupil(s) of the eye(s) of the patient 106.

In various examples, as described herein with reference to FIGS. 2 and 3A-3D, the vision screening device 200, 300 may include NIR radiation sources(s) and sensor(s) to capture NIR images of the eye(s) of the patient, as well as white light source(s) and color camera to capture color images of the eye(s) of the patient. The vision screening device 200, 300 may also capture images of the eye(s) while under illumination from radiation source(s) at different angles with respect to the optical axis of the eye(s). While the radiation source(s) 114, 210, 308 have been described as comprising infrared or near-infrared (NIR) radiation source(s), in additional examples, the radiation source(s) 114, 210, 308 may include LEDs emitting radiation at different wavelengths, and the radiation sensor(s) 116, 212, 310 may capture image(s) of the eye(s) while illuminated by radiation at different wavelengths and/or different wavelength bands (e.g., infrared, NIR, visible light, ultra-violet, etc.). The different wavelengths of radiation in the visible spectrum may include wavelengths corresponding to specific colors. In such examples, the vision screening device 104, 200, 300 may be able to detect diseases and/or abnormalities of the eye(s) that may be more apparent in images captured under illumination of specific wavelengths. In addition, since colored light and white light are also forms of electromagnetic radiation, the term "radiation source" as used herein, may refer to both visible light emitters as well radiation emitters in the infrared/NIR, and ultra-violet ranges of the electromagnetic spectrum.

FIGS. 4A-4D illustrate images of eyes captured by the radiation sensor(s) 116, 212, 310 or the camera 120, 216, 312b of the vision screening device 104, 200, 300. Various abnormalities and/or diseases of the eye(s) that may be detected utilizing analysis of image data captured by the vision screening device 104, 200, or 300 are discussed herein with reference to FIGS. 4A-4D. FIG. 4A illustrates an image 402 of the eyes of a patient with normal eye health and no detectable disease conditions or abnormalities. The image 402 includes the right eye 404a and the left eye 404b of the patient. As shown, the iris 406a and pupil 408a of the right eye 404a appear substantially similar to the corresponding iris 406b and pupil 408b of the left eye 404b in patients exhibiting normal eye health. As described with reference to FIG. 1, the data analysis and visualization component 136 may process the captured images to determine location of pupils of the eye(s), and generate images of the pupils (e.g., pupil images). Since the pupils allow radiation to enter the interior of the eye and reflected radiation to return out of the eye after interaction with different layers of the eye, the pupil images capture the appearance of layers of the eye(s), such as cornea, lenses, aqueous and vitreous humors, and retina which are illuminated by the radiation impinging on the eye. U.S. patent application Ser. No. 17/347,079, filed on Jun. 14, 2021, the entire disclosure of which is incorporated herein by reference, describes example systems and methods for detecting pupil images captured under different illumination patterns generated by near-infrared (NIR) radiation sources for determining refractive error based on photorefraction.

FIG. 4B illustrates an example image 410 of a disease condition that may be detected by comparing a pupil image 412a of one eye 414a with a pupil image 412b of the other eye 414b. The image 410 may be a grayscale image captured by the radiation sensor(s) 116, 212, 310 under NIR illumination, and illustrates an example of a difference in grayscale in the images of the left and right eye as a result of media opacity or a clouding of the lens typical of cataract development. As described with reference to FIG. 1, the data analysis and visualization component 136 may compare pupil images of the left and the right eyes to determine a difference in grayscale value between the eyes. For example, the image 410 may have grayscale values of 0 to 128, and the average grayscale value in the pupil portion of the image in one eye may be 24, whereas in the other eye it may be 80. The computed difference may be compared with threshold(s) and/or ranges in standard test data corresponding to normal eyes to determine if an abnormality is present. However, a grayscale image, such as the image 410, may be unable to capture differences between the eyes corresponding to some diseases and abnormalities that may be easily discernible from a color image. For example, tumors of the retina or cornea of the eye may appear as a uniform gray area similar to the appearance of a normal retina in a grayscale image captured under NIR illumination.

FIG. 4C illustrates a color image 416 captured under white light illumination (e.g., from white light source(s) 118, 214, 312a), by the camera(s) 120, 216, 312b of the vision screening device 104, 200, 300. Since the pupil images 420a, 420b of the image 416 are generated from white light reflected back from the retina of the eyes, and through the cornea, diseases and abnormalities of the retina and cornea may be visible in such an image. For example, since the retina is highly vascular, the reflected light may appear to be of an orange-red color in a healthy eye, but may appear to be white or yellowish in an eye with a retinal or corneal tumor. While there may be variations in the appearance of the color of the pupil images 420a, 420b due to different pigmentations of the retina among patients of different ethnicities, comparisons between the two pupil images 420a and 420b of the same patient may reliably produce differences in color values when the disease or abnormality is present in only one of the two eyes. As described with reference to FIG. 1, the data analysis and visualization component 136 may compare pupil images of the left and the right eyes to determine a difference between color values. The data analysis and visualization component 136 may also compare the color values of each pupil image with standard images of pupils of healthy eyes. The image 416, as captured by the camera(s) 120, 216, 312b, may be a typical digital color image where each pixel indicates an RGB (red, green, blue) value in a range of 0-256 for each of the three color channels. As is known in the art, the RGB color space is often unsuitable for applications requiring a determination of difference between colors due to its sensitivity to variation in lighting and poor correlation between distances between colors in the RGB color space and perceptual differences between the colors. In examples, the color image 416 may be transformed into a color space more suited for determining differences between colors (e.g., CIE L*a*b*, CIE L*u*v*, CIE 1931 model, HSI (hue, saturation, intensity), and the like). The difference between an average color value of the pupil image 420a and an average color value of the pupil image 420b may be determined in the transformed color space. In some examples, the difference in color values between the eyes of a patient may be further adjusted to remove effects of refractive error of the eye(s) that may also cause differences in the appearance of the pupils, using a measurement of the refractive error of the eye(s). A difference value that is greater than a threshold and/or outside a range in standard data corresponding to normal healthy eyes may be flagged as a detected abnormality. For example, color differences illustrated in image 416 may be a result of tumors in one of the eyes such as a retinoblastoma.

FIG. 4D further illustrates an image 422 of the eyes 424a, 424b, including pupil images 426a, 426b. The image 422 may be grayscale image captured by the radiation sensor(s) 116, 212, 310 under NIR illumination or a color image captured by the camera(s) 120, 216, 312b under white light illumination. As shown, even though the average grayscale value or the average color value may be similar in images of pupil 426a and 426b, there may be other types of differences between them, such as, non-uniformities, inclusions, or other structures, which may be indicative of a disease condition and/or abnormalities. For example, small non-uniformities or inclusions may be indicative of early stages of cataract formation, presence of foreign bodies in media of the eye, scratches in the cornea or lens, and the like. The data analysis and visualization component 136 may determine these types of differences between pupil images 426a and 426b by various methods. For example, an alignment of the pixel images 426a and 426b, followed by a subtraction of pixel values of pixels at corresponding locations would result in a difference image primarily indicating areas of differences. A summation of pixel values of the difference image may be compared with a threshold to determine if the difference is higher than the threshold (e.g., in an instance of abnormalities). The data analysis and visualization component 136 may also determine differences by computing variance in grayscale or color values within the pupil image 426b. If the variance is higher than a threshold, or outside a range expected in a healthy eye, an abnormal condition may be determined.

In some examples, the data analysis and visualization component 136 may determine some conditions of the eyes by evaluating each pupil image, taken individually, for uniformity of characteristics in the pupil image. The characteristics may include color, brightness, texture, etc. For example, the data analysis and visualization component 136 may determine standard deviation (or variance) in the characteristic within the pupil image, and if the standard deviation is higher than a threshold, or outside a range expected in a healthy eye, an abnormal condition may be determined.

Though FIGS. 4A-4D show examples of some conditions of the eyes that may be determined by the techniques discussed herein, it should be understood that additional conditions may also be determined. In addition, the data analysis and visualization component 136 may analyze a color image under white light illumination, a grayscale image under NIR illumination, and/or a composite image (as described with reference to FIG. 1), to determine a condition of the eyes. For example, a presence of a cataract in the eye(s) may be determined based on the composite image, whereas a presence of a blastoma may be primarily determined based on the color image. In some examples, the color image and/or the grayscale image may be extracted from a color and/or grayscale video of the eyes e.g., one or more frames of the video.

As discussed herein, FIGS. 4A-4D illustrates processing of images captured by the radiation sensor(s) 116, 212, 310 and/or the camera(s) 120, 216, 312b that may be performed by the data analysis and visualization component 136 of the vision screening device 104 in order to determine differences between pupil images indicative of disease conditions and/or abnormalities of the eye(s) of the patient. Other examples of processing tailored for detecting specific disease conditions and abnormalities are also envisioned. For example, images captured under different wavelengths of radiation may be used for detecting signature differences in grayscale or color values or structure of images indicative of specific disease conditions.

Figures 5A, 5B:
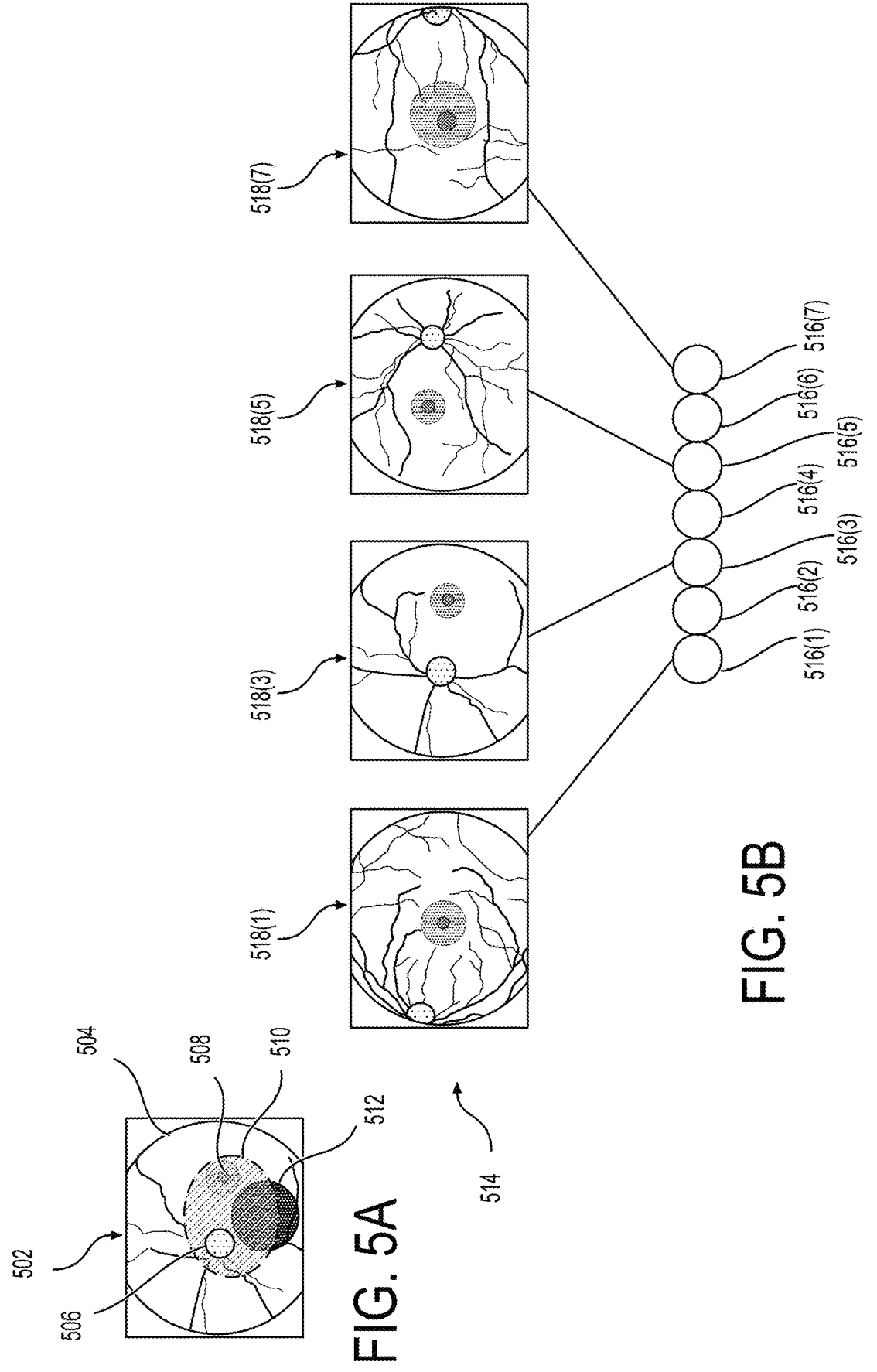
FIG. 5A and FIG. 5B illustrate example visualizations generated by a vision screening device of the present disclosure.

FIGS. 5A and 5B illustrate example visualizations of pupil images that may be generated by the vision screening device 104, 200, or 300. As described with reference to FIG. 1, the data analysis and visualization component 136 may process the captured pupil images and generate one or more visualizations that may aid a clinician or an operator of the vision screening device to diagnose abnormalities or diseases in the eyes of the patient (e.g., the patient 106). As described, the first visualization may generate a composite image 502 that incorporates information from grayscale image(s) captured by the radiation sensor(s) 116, 212, 310 under NIR illumination and color image(s) captured by the camera(s) 120, 216, 312b under white light illumination. The data analysis and visualization component 136 may align the grayscale image(s) and the color image(s) so that the pupil 504 of the eye in the images overlap each other e.g., perform an image registration step. The data analysis and visualization component 136 may then perform an image registration step of higher accuracy based on specific features of the eyes such as optic disc 506 and/or fovea 508, so that the grayscale image(s) and the color image(s) are accurately aligned e.g., when the features of the eyes overlap each other. In some examples, the registration steps may be performed even when the vision screening device is not moved between image captures because small movements by the patient or eye motion of the patient may result in misalignment between images.

In examples, the composite image 502 may be generated from the aligned grayscale and color images e.g., by the data analysis and visualization component 136, to include pixel values from the grayscale image(s) in some portion(s) 510 and pixel values from the color images in the rest of the pupil area 504. The selection of the image to incorporate in different portions of the composite image 502 may be based on whether features in that portion are easier to discern under NIR illumination or under white light illumination. For example, the portion 510 of the eye may include features or a condition that is better discerned under NIR illumination, whereas a vascular structure in the rest of the pupil image 504 may be clearer in the color image(s) captured under white light illumination. In such an example, the data analysis and visualization component 136 may use grayscale values from the grayscale image(s) in the area 510 of the composite image 502, and color values form the color image(s) in the rest of the pupil image 504 to generate the composite image 502. In instances where multiple grayscale images and color images have been captured, the data analysis and visualization component 136 may use an average grayscale value at each pixel location across the grayscale images, and an average color value at each pixel location across the color images to create a merged grayscale image and a merged color image. In other examples, a single image may be selected from the multiple images for use in the composite image 502 based on factors such as image quality (e.g., sharpness, angle of illumination, or visibility of a particular feature of the eye). As described above, the composite image derives a first plurality of pixel values from the grayscale image(s) captured under NIR illumination, and a second plurality of pixel values from the color image(s) captured under white light illumination. Therefore, the composite image includes properties of the eye as revealed by NIR and visible light illumination independently.

In some examples, the composite image may include portions of the face of the patient in addition to the eyes (e.g., nose, forehead), or even the full face. In some examples, additionally or alternatively, the data analysis and visualization component 136 may also add a graphic 512 (e.g., in pseudo-color), to the composite image 502 to highlight portions or areas of the composite image 502 where differences were detected between the left and right pupil images, or between the captured image and a standard image. In some examples, colors used in highlighting (e.g., within the graphic 512), may be based on a heatmap visualization scheme where cooler or blue hues may indicate smaller differences and warmer or red hues may indicate larger differences. Portions of the composite image 502 where the differences exceed a standard threshold or are outside a standard range may be assigned a pseudo-color from the highest end of the heatmap. Other features of the eye may also be highlighted using different graphics or different color legends. In such examples, a clinician or an operator may have an option to turn the highlighting and/or graphics on or off or toggle between the two, to aid in diagnosis of the condition of the eye. The composite image 502 may be stored in a database (e.g., the screening database 144) as a part of the patient data 140.

FIG. 5B illustrates a visualization 514 comprising a sequence of still images or an animated video comprising the sequence of still images. This visualization may correspond to the second visualization as described with reference to the data analysis and visualization component 136 of FIG. 1. Radiation sources 516(1-7) may correspond to NIR LEDs along axes or meridians 316, 318 or 320 of FIG. 3B, for example. Alternatively or in addition, the radiation sources 516(1-7) may comprise an array of white light LEDs of the white light source(s) 118, 214, 312a. Pupil images 518(1-7) indicate images captured by radiation sensor(s) 116, 212, 310 or by the camera(s) 120, 216, 312b under illumination from the corresponding radiation source 516 (1-7). For example, the image 518(1) may be captured while the radiation source 516(1) is active, the image 518(3) may be captured while the radiation source 516(3) is active, and so on. It is to be noted that the sequence 514 may not include images corresponding to each radiation source (e.g., 516(2, 4, 6)). In examples, any number of the images corresponding to the radiation source(s) 516(1-7) may be used in the generation of the visualization 514. In addition, more or fewer radiation source(s) 516 are also envisioned.

As described above with reference to FIG. 5A, images captured under illumination from the individual radiation sources (e.g., 516(1,3,5,7)) are aligned so that the pupils appear in the same location relative to the overall image in each of the images. This alignment step or registration prevents jitter when the images are presented in a sequence (e.g., on the display screen 122, 220). The visualization 514 may comprise presenting the images 518(1-7) in order on the display screen 122, 220 from left to right (e.g., as sequence of images 518(1), 518(3), 518(5), 518(7)), and/or from right to left (e.g., as sequence of images 518(7), 518(5), 518(3), 518(1)). In addition, the data analysis and visualization component 136 may generate an animated video where each frame of the video comprises a single image in the sequence. The animated video may comprise displaying the sequence from left to right, followed by the sequence from right to left, repeatedly, to create an appearance of the illumination source moving back and forth from end to end. The vision screening device may present a graphical user interface (e.g., on the display screen 122, 220), that allows the clinician or operator of the vision screening device to pause the video on any frame, and/or zoom in or out. In addition, the visualization 514 may use the grayscale image captured under NIR illumination, the color image captured under white light illumination, or the composite image described above with reference to FIG. 5A as each image 518(1,3,5,7). The graphical user interface may provide an option of viewing the grayscale image, the color image, or the composite image.

In various examples, as described herein with reference to FIGS. 5A and 5B, the vision screening device 300 may provide an operator of the vision screening device 300 with visualizations to aid in the diagnosis of diseases and/or abnormalities of the eye(s) of the patient. In addition, these visualizations may be stored (e.g., in the screening database 144), as a part of patient data 140, so that the visualizations may be accessed by clinicians for review, or for comparison during future vision screening tests of the same patient.

Figure 6:
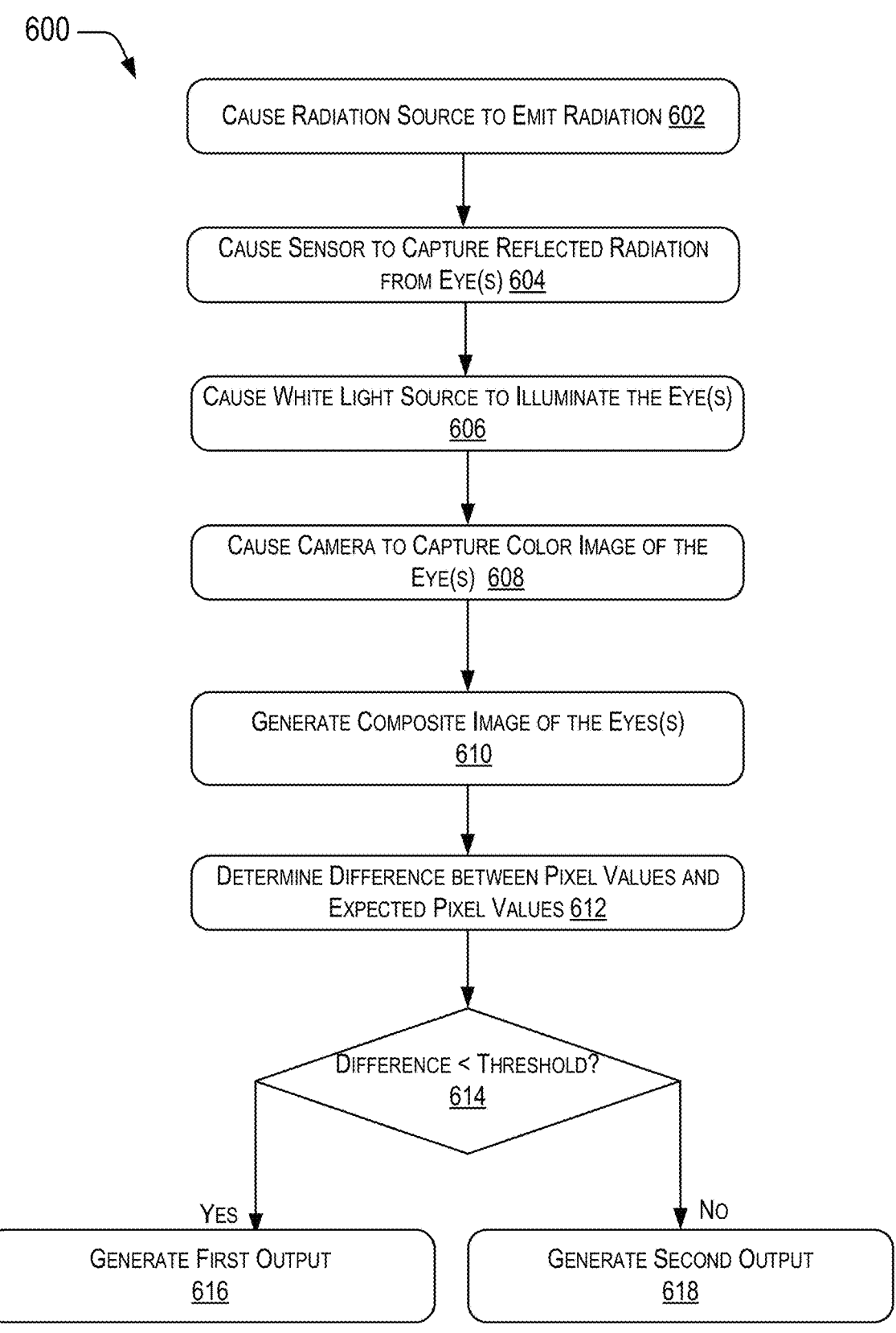
FIG. 6 provides a first flow diagram illustrating an example method of the present disclosure.
Figure 7:
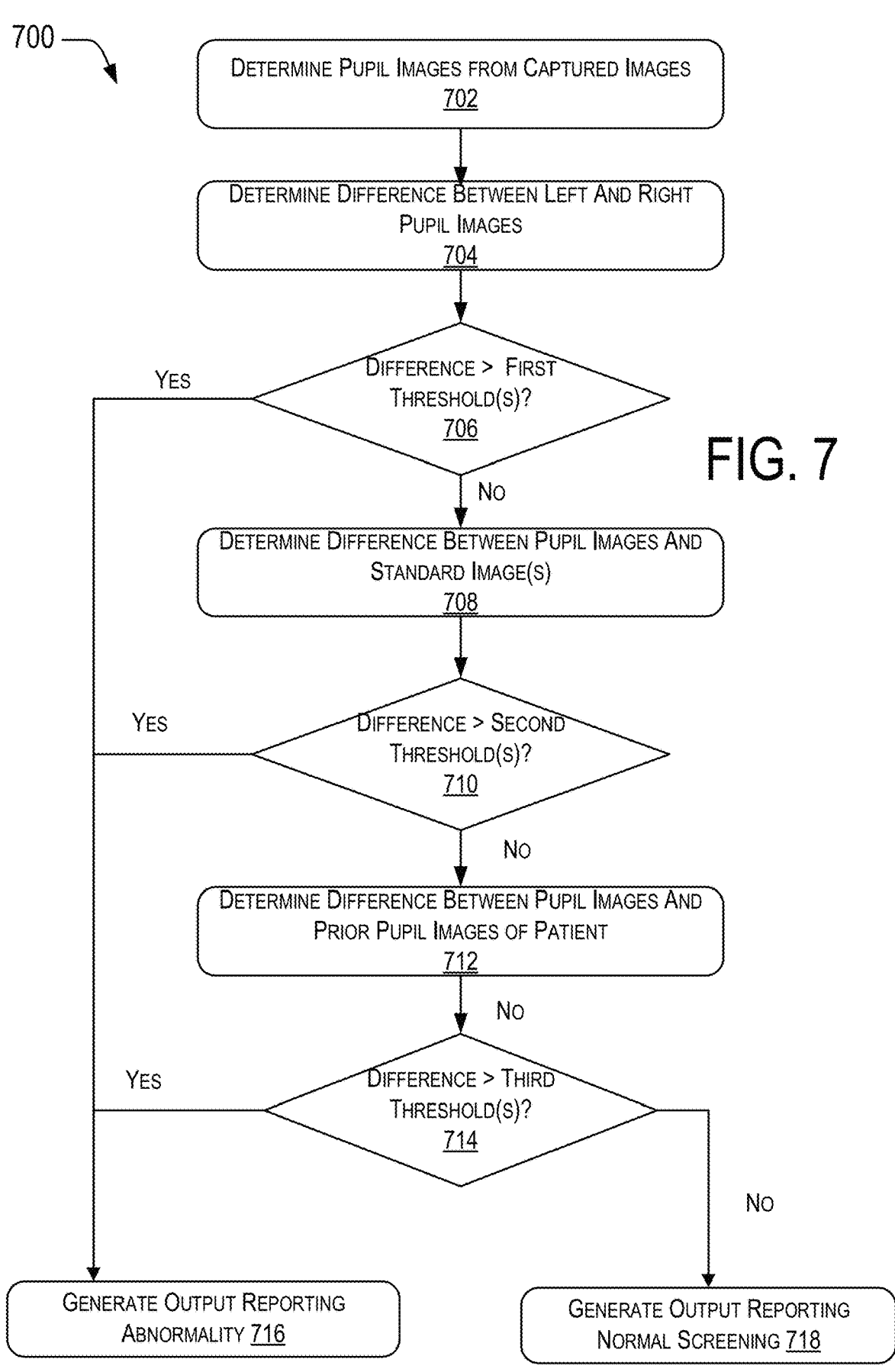
FIG. 7 provides a second flow diagram illustrating an example method of the present disclosure.
Figure 8:
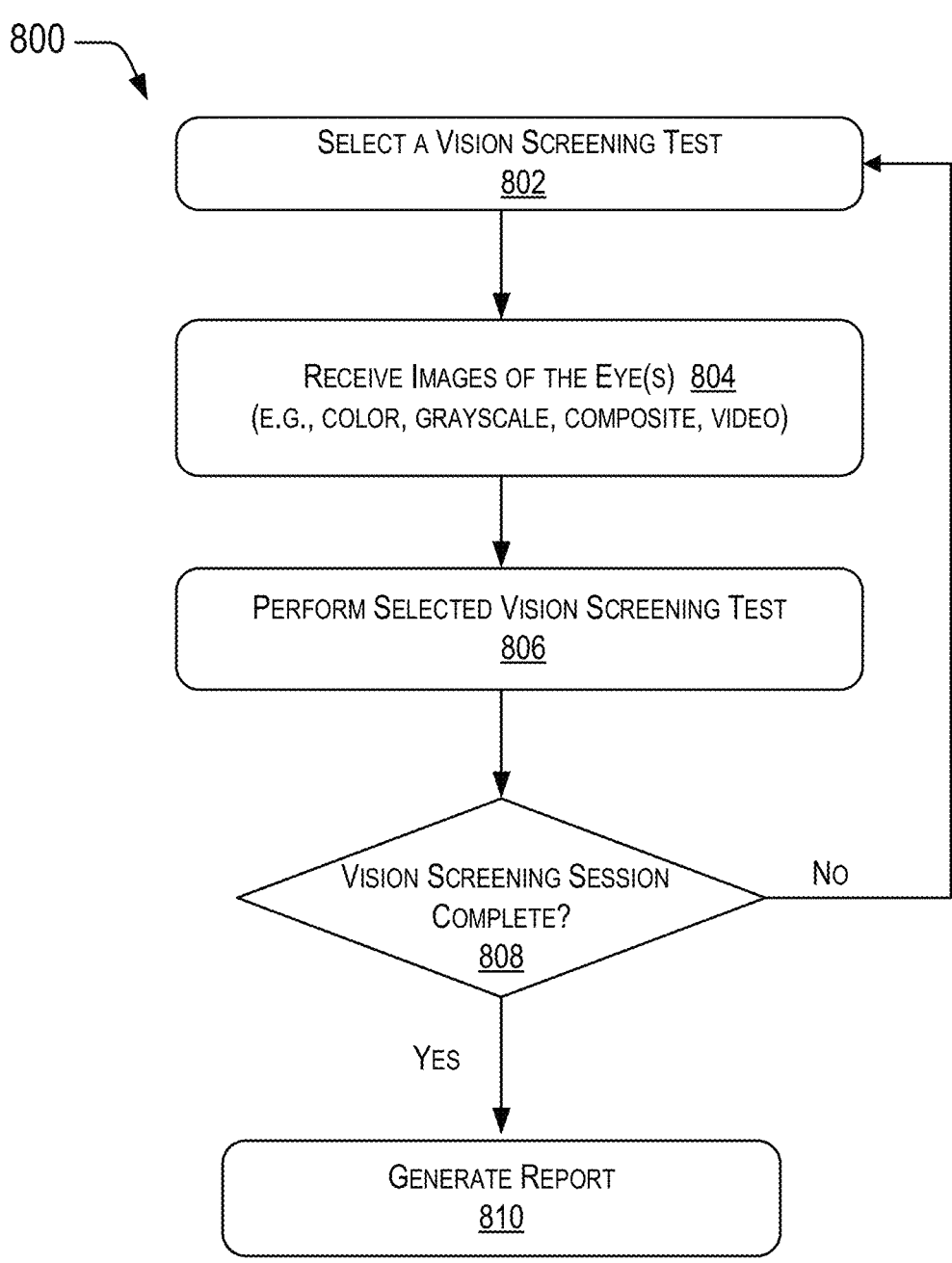
FIG. 8 provides a third flow diagram illustrating an example method of the present disclosure.

FIGS. 6-8 provide flow diagrams illustrating example methods for vision screening, as described herein. The methods in FIGS. 6-8 are illustrated as collections of blocks in a logical flow graph, which represents sequences of operations that can be implemented in hardware, software, or a combination thereof. In the context of software, the blocks represent computer-executable instructions stored on one or more computer-readable storage media that, when executed by processor(s), perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the methods illustrated in FIGS. 6-8. In some embodiments, one or more blocks of the methods illustrated in FIGS. 6-8 can be omitted entirely.

The operations described below with respect to the methods illustrated in FIGS. 6-8 can be performed by any of the devices or systems 104, 200, and 300 described herein, and/or by various components thereof. Unless otherwise specified, and for ease of description, the methods illustrated in FIGS. 6-8 will be described below with reference to the system 100 shown in FIG. 1, and the vision screening device 104, 200, 300 of FIGS. 1-3. In particular, any of the operations described with respect to the methods illustrated in FIGS. 6-8 may be performed by the image capture control component 134, the data analysis and visualization component 136, and/or the output generation component 138 executed by the processor(s) 128 of the vision screening device 104 and/or by the analysis component 150 executed by the processor(s) 146 of the vision screening system 110, either alone or in combination.

With reference to the example method 600 illustrated in FIG. 6, at operation 602, the image capture control component 134 and/or one or more processors associated therewith may cause a radiation source to emit radiation (e.g., near-infrared (NIR) radiation). For example, the radiation source may comprise NIR LEDs of the radiation source(s) 114 of the vision screening device 104, configured to emit NIR radiation during a period of time corresponding at least in part to the administration of a vision screening test indicated for the patient by the patient screening component 132. In some examples, the image capture control component 134 may cause radiation of different wavelengths to be emitted e.g., a first radiation source may emit radiation of a first wavelength, and a second radiation source may emit radiation of a second wavelength. The image capture control component 134 may activate LEDs of the radiation source(s) 114 individually or in groups to produce radiation impinging on the eyes at different angles relative to the optical axis of the eye, as described with reference to FIG. 3B. For example, the image capture control component 134 may set a pattern of activation of the NIR LEDs along the axes 316, 318, and 320 as described above with reference to FIG. 3B. In addition, the image capture control component 134 may activate different wavelengths of radiation combined with different angles of incidence on the eyes. In some examples, the arrangement of the pattern of activation of the NIR LEDs allows for different illumination patterns to be presented to the eye(s) of the patient 106, and refractive error of the eye(s) may be accurately measured based on images captured under the illumination pattern selected. Additional details regarding illumination patterns used in examination protocols for determining refractive error can be found in U.S. Pat. No. 9,237,846, referred to above and incorporated herein by reference.

At operation 604, the image capture control component 134 may cause a sensor of the vision screening device (e.g., radiation sensor(s) 116 of the vision screening device 104), to capture radiation reflected by the eye(s) of the patient under illumination by the radiation source(s) 114. The image capture control component 134 may receive data indicative of the radiation captured by the radiation sensor(s) 116. The data may include grayscale image(s) and or video of the eye(s) illuminated by radiation from different angles as described above at operation 602. For example, the image capture control component 134 may cause a sensor to capture a first image under illumination from a first set of NIR LEDs, and a second image under illumination from a second set of NIR LEDs. In some examples, near-infrared may be a first wavelength band emitted by a first radiation source(s), and the image capture control component 134 may further activate a second radiation source(s) emitting radiation in a second wavelength band, and cause a sensor to capture a third image under illumination from the second radiation source. In addition, the image capture control component 134 may cause the sensor(s) to capture images of both eyes simultaneously, or one eye at a time. For example, the image capture control component 134 may change the activation of the illumination source(s) (e.g., activate different LEDs of the radiation source(s) 114, 118) after capturing an image of the left eye and before capturing an image of the right eye, so that both the left and right eye are illuminated from a same angle relative to the eye during the image capture. In some examples, the image capture control component 134 may cause the sensor to capture multiple images of the eyes while the patient 106 is directed to look in different directions e.g., the patient's 106 gaze direction may be to the left, right, up and/or down with respect to an optical axis of the vision screening device 104.

At operation 606, the image capture control component 134 and/or one or more processors associated therewith may cause a white light source (e.g., white light source(s) 118 of the vision screening device 104), to emit white light to illuminate the eye of the patient during a period of time after the operation 602 and 604 are completed, and during at least a part of the administration of the vision screening test. Similar to the radiation source(s) described at operation 602, individual white light sources of the white light source(s) 118 may also be activated to illuminate the eye from different angles relative to the optical axis. In some examples, the illumination from the white light source(s) 118 may be coaxial or near-coaxial with the optical axis e.g., the angle may be substantially zero degrees. In some examples, at operation 606 or in other operations of the method 600, the image capture control component 134 may cause the sensor(s) to capture multiple images of the eyes corresponding to different gaze directions of the patient 106 as described above e.g., a first color image of the eye(s) may be captured corresponding to a first gaze direction of the patient and a second color image of the eye(s) may be captured corresponding to a second gaze direction of the patient. In some examples, the images captured at operation 606 or at other operations of the method 600 may include still images and/or video. The image capture control component 134 may store, as metadata associated with an image, a time of capture and the angle of illumination and/or the gaze direction of the patient at the time of capture of the image. It is understood that any of the images and/or video captured at operation 606 or at other operations of the method 600 may be used to identify, diagnose, and/or otherwise evaluate various disease states of the patient.

For example, at operation 608, the image capture control component 134 may cause a camera (e.g., the camera 120 of the vision screening device 104), to capture color image(s) of the eye(s) of the patient while under white light illumination. In some examples, the image capture control component 134 may also cause the camera to capture video data. For example, video data may be captured during a first period of time before onset of white light illumination, and continue during a second period of time after commencement of the white light illumination. For example, the video data may be useful for determining a reaction of the patient's pupils (e.g., size of the pupils) and/or an adjustment of the pupils to varying levels of illumination and/or a sharp change in illumination (e.g., caused by onset of the white light illumination). The image capture control component 134 may store the color image(s) and/or video in a database for review by a clinician. In addition, the image capture control component 134 may cause the camera to capture a color image of the patient's face and store the image in the patient data 140 as a photo identifier of the patient. The data analysis and visualization component 136 may utilize the color image(s) to generate a composite color image, and determine differences at operations 610 and 612, as described below. In some examples, the composite color image may be generated by combining color images captured at different gaze directions of the patient to illustrate a retina of the eye(s).

At operation 610, the data analysis and visualization component 136 may generate a composite image of the eye(s) by combining information from the grayscale image(s) captured at operation 604 and the color image(s) captured at operation 608. As described above with reference to FIG. 5A, the data analysis and visualization component 136 may detect pupil images corresponding to the pupils of the eye(s) in the grayscale image(s) and the color image(s), and align the grayscale and color pupil images so that structures of the eyes overlap. The data analysis and visualization component 136 may further generate the composite image incorporating grayscale values from the grayscale image(s) in a portion of the composite image, and color values from the color image(s) in the rest of the composite image. The data analysis and visualization component 136 may also annotate (e.g., using graphics and/or pseudo-color values) some portions of the composite image to indicate areas of interest, for example.

At operation 612, the data analysis and visualization component 136 or the output generation component 138 may determine one or more differences between pixel values and expected pixel values in the grayscale, color, and/or the composite image(s). For example, the data analysis and visualization component 136 or the output generation component 138 may compute a first difference as an average difference between pixel values at corresponding pixel locations in the left and right pupil images of the patient. As another example, the data analysis and visualization component 136 or the output generation component 138 may compute a second difference between average pixel values in a first area of a pupil image and a second area of the same pupil image. In yet another example, the data analysis and visualization component 136 or the output generation component 138 may compute a third difference between average pixel values in a pupil image and standard values from normal, healthy eyes which may be stored in a database (e.g., the screening database 144). Further, the data analysis and visualization component 136 or the output generation component 138 may compute a fourth difference between pixel values in the pupil images captured during the vision screening test and pupil images of the same patient captured during previously administered vision screening test(s).

At operation 614, the output generation component 138 may compare the difference(s) in pixel values obtained at operation 612 with threshold value(s) and/or range(s) to determine an output indicative of a condition associated with the eye(s), which may include a diagnosis or recommendation. For example, if the difference is less than the threshold value (Operation 614—Yes), the output generation component 138 may generate a first output associated with the patient at operation 616, and if the difference is equal to or higher than the threshold value (Operation 614—No), the output generation component 138 may generate a second output at operation 618. The threshold value(s) and/or range(s) may be predetermined and available as a part of standard data, which may be stored in the screening database 144 or the computer-readable media 130, 148. The standard data may include different threshold(s) and range(s) for each type of the differences described above, including separate thresholds and ranges for grayscale and color values. The threshold(s) and range(s) may also be different based on the testing category of the patient (e.g., the patient's age group, or medical history).

At operation 616, the output generation component 138 may generate the first output as described above (Operation 614—Yes). The first output may correspond to an indication that a disease or abnormality was detected, a recommendation of additional screening, and/or a diagnosis of a disease or abnormality detected. The first output may also include links to stored images, including captured grayscale and color images and/or generated visualizations. At operation 618, the output generation component 138 may generate the second output (when Operation 614—No). The second output may correspond to an indication of that the patient has passed the vision screening, or that the patient's eye(s) appear normal and healthy.

As discussed, the example method 600 may be performed by the components of the vision screening device 104 executed by the processor(s) 128 of the device 104. The example method 600 illustrates operations performed during at least a part of a vision screening test administered to a patient (e.g., the patient 106) to determine diseases and/or abnormalities associated with the eye(s) of the patient based on images of the eye(s) captured under illumination of different wavelengths. In alternative examples, some or all of the operations of method 600 may be executed by processor(s) 146 of a vision screening system 110 that is connected to the vision screening device 104 via network 108.

FIG. 7 illustrates an example method 700 for vision screening according to some implementations of the present disclosure. As discussed, the operations of the process 700 will be described as being performed by the processor(s) 128 the vision screening device 104, even though the operations may also be alternatively or additionally performed by the processor(s) 146 of the remote vision screening system 110.

At operation 702, the data analysis and visualization component 136 may determine pupil images from captured images. As discussed, the captured images may include grayscale image(s) captured by the radiation sensor(s) 116, 212, 310 under NIR illumination or color image(s) captured by the camera(s) 120, 216, 312b under white light illumination. Pupil images may be determined from images captured under NIR radiation illumination using the techniques described in U.S. Pat. No. 9,237,846, referred to above and incorporated herein by reference. The data analysis and visualization component 136 may also determine pupil images from color images using various techniques e.g., by detecting edges using image processing techniques, followed by arc fitting, and comparing the detected edge arcs with a model edge map of an eye image. Pupil images may also be determined from color images using color of the pupil to segment the pupil area of an image of the eye(s). A combination of edge and color-based segmentation may also be used.

At operation 704, the data analysis and visualization component 136 may determine difference(s) between the left and the right pupil images of the patient. The differences may be determined using grayscale values of the grayscale image(s) and/or color values of the color image(s). As described with reference to operation 612 of FIG. 6, the difference may be computed as an average difference between pixel values at corresponding pixel locations in the left and right pupil images of the patient, or corresponding portions in the left and right pupil images of the patient. In other examples, the data analysis and visualization component 136 may determine the difference by summation of the pixel values obtained by the subtraction of the left pupil image from the right pixel image, or vice versa.

At operation 706, the data analysis and visualization component 136 may compare the difference obtained at operation 704 with a first threshold to determine whether the difference is less than the first threshold value. For example, the first threshold value may be predetermined and available as a part of standard data, which may be stored in the screening database 144, and indicate a maximum difference expected between two pupil images of the same patient when a patient exhibits normal, healthy eyes. If the difference is equal to or greater than the first threshold (Operation 706—Yes), the output generation component 138 may generate an output reporting an abnormality at operation 716, as described in more detail below.

At operation 708 (Operation 706—No), the data analysis and visualization component 136 may determine difference(s) between the left or the right pupil images of the patient and standard image(s) of normal, healthy eyes. The left and the right pupil images may be captured simultaneously, or at different times during the vision screening test. Standard image(s) may be available as a part of standard data, which may be stored in the screening database 144 or the computer-readable media 130, 148.

At operation 710, the data analysis and visualization component 136 may compare the difference obtained at operation 708 with a second threshold to determine that the difference is less than the second threshold value. For example, the second threshold value may also be predetermined and available as a part of standard data stored in the screening database 144, and indicate a maximum difference expected between a pupil image and a standard image of normal, healthy eyes. If the difference is equal to or greater than the second threshold (Operation 710—Yes), the output generation component 138 may generate an output reporting an abnormality at operation 716, as described in further detail below.

At operation 712 (Operation 710—No), the data analysis and visualization component 136 may determine difference(s) between a pupil image of the patient and a pupil image of the same eye captured during prior vision screening test(s). Pupil images of the patient captured during prior vision screening test(s) (e.g., annual screening tests from previous years), may be stored as a part of the patient data 140 in a database (e.g., the screening database 144). The data analysis and visualization component 136 may access the pupil images from the previous screening test(s) from the database, and/or load the images into the computer readable media 130 prior to the start of the current vision screening test.

At operation 714 (Operation 712—No), the data analysis and visualization component 136 may compare the difference obtained at operation 712 with a third threshold to determine that the difference is less than the third threshold value. For example, the third threshold value may be predetermined and available as a part of standard data, which may be stored in the screening database 144, and indicate a maximum difference expected between pupil images of the same eye captured after a duration of time. If the difference is equal to or greater than the third threshold (Operation 714—Yes), the output generation component 138 may generate an output reporting an abnormality at operation 716. For example, the output may indicate a change in the eye of the patient, which may be due to a progressive eye disease, such as cataracts or macular degeneration, or a new disease condition not present during the previous screening test(s).

At operation 716, the output generation component 138 may generate an output reporting an abnormality. As discussed above, if any of the difference(s) determined at operations 704, 708, 712 are greater than or equal to their respective thresholds, the data analysis and visualization component 136 or the output generation component 138 may determine that a possible abnormality and/or disease condition may be present in the eye(s). The output may also include a diagnosis based on the difference that triggered the reporting of abnormality. As described with reference to FIG. 4, specific diseases may exhibit signature differences in the appearance of the pupil images, and some diseases, such as retinoblastoma, cataracts, scratched cornea and the like, may be determined from the differences detected during the vision screening test(s). The output generation component 138 may store the output as a part of the patient data 140 in a database, such as the screening database 144. The output generation component 138 may also display the output to an operator (e.g., the operator 102) on a display screen (e.g., the display screen(s) 122, 220, 334).

In the absence of any difference meeting or exceeding the respective thresholds, at operation 718, the output generation component 138 may generate an output reporting a normal screening e.g., that the eye(s) of the patient were determined to be normal based on the vision screening test(s). The output generation component 138 may store the output as a part of the patient data 140 in a database, such as the screening database 144, and/or may display the output to an operator of the vision screening device (e.g. the operator 102) on the display screen(s) 122, 220, 334.

FIG. 8 illustrates an example method 800 for vision screening according to some implementations of the present disclosure, where the vision screening includes one or more separate vision screening tests e.g., each screening for a different condition of the eye(s). Various operations of the method 800 may be substantially similar to or the same as the methods described with reference to FIG. 6 and FIG. 7. As discussed, the operations of the process 800 will be described as being performed by the processor(s) 128 the vision screening device 104, even though the operations may also be alternatively or additionally performed by the processor(s) 146 of the remote vision screening system 110.

At operation 802, the patient screening component 132 may select a vision screening test to perform on a patient participating in a vision screening session. As discussed with reference to FIG. 1, the patient screening component 132 may determine a list of vision screening test(s) to administer to the patient based at least in part on the testing category of the patient (e.g., the age group or medical history of the patient) as stored in the patient data 140. The vision screening test selected at the operation 802 may be a next incomplete vision screening test on the list of vision screening tests to be administered to the patient. In some examples, at 802, the patient screening component 132 may select the vision screening test based on an input received from a clinician or an operator administering the screening tests.

At operation 804, the data analysis and visualization component 136 may receive, from the image capture control component 134, images of the eye(s) of the patient undergoing vision screening. For example, the images may include one or more of grayscale images captured under NIR radiation illumination, color images captured under white light illumination, color or grayscale video, and/or composite images. The images may be captured as described with reference to the example method 600 illustrated in FIG. 6. In some examples, the images may be previously captured e.g., while administering a previously selected vision screening test, and no new images may be captured.

At operation 806, the data analysis and visualization component 136 may perform the selected vision screening test e.g., using the method 700 described with reference to FIG. 7. Each vision screening test may have a pre-determined set of image requirements associated with it, indicating the image(s) most suitable for detecting the condition being screened for. For example, the image requirements may include a type of image (e.g., color, grayscale, composite, video etc.), angle(s) of illumination or gaze direction(s), type/level of illumination etc. The data analysis and visualization component 136 may identify image(s) to analyze based on the image requirements e.g., by matching the image requirements to metadata associated with the captured image(s), and perform the selected vision screening test based on analysis of the identified image(s). For example, a screening test for presence of a cataract in the eye(s) may require the composite image, whereas a screening test for presence of a blastoma may require be the color image as input. In some examples, image(s) captured at different illumination angles or gaze directions may be extracted from video e.g., by identifying frames associated with the required illumination angles or gaze directions.

At operation 808, the patient screening component 132 may determine whether the vision screening session is complete e.g., the vision screening test performed at operation 806 was last on the list of vision screening test(s) determined by the patient screening component 132. If, at 808, the patient screening component 132 determines that the vision screening session is not complete (Operation 808—No), the patient screening component 132 may proceed to operation 802 to select a vision screening test to be performed next. On the other hand, if at 808 the patient screening component 132 determines that the vision screening session is complete (Operation 808—Yes), the output generation component 138 may generate a report, at operation 810, including results of the vision screening test(s) performed during the vision screening session. For example, the report may include one or more of the output(s) described above with respect to the operations 716, 718 of method 700, for each vision screening test performed during the vision screening session.

Based at least on the description herein, it is understood that the vision screening devices and associated systems and methods of the present disclosure may be used to assist in performing one or more vision screening tests, including test(s) to screen for diseases and/or abnormalities of the eye(s) of the patient. The components of the vision screening device described herein may be configured to generate radiation of different wavelengths, in addition to white light, to illuminate the eyes of the patient undergoing vision screening, capture image(s) of the eye(s) under different illumination conditions, generate visualizations that aid in the diagnosis of disease conditions, determine differences between pupil images, and determine an output indicating a diagnosis, recommendation or results of the screening test. An exemplary vision screening device may include radiation source(s) for generating radiation of different wavelengths, and sensor(s) for capturing the reflected radiation from the eye(s) of the patient, a white light source and a camera configured to capture color image(s) of the eye(s) of the patient under white light illumination, and display screen(s) for displaying the output to an operator of the vision screening device. The device described herein may be used for screening a patient for ocular diseases and abnormalities without requiring inputs or feedback from the patient, and without requiring dilation of the eyes, thereby allowing the device to be used for screening very young, very old, incapacitated, or uncooperative patients.

The foregoing is merely illustrative of the principles of this disclosure and various modifications can be made by those skilled in the art without departing from the scope of this disclosure. The above described examples are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

As a further example, variations of apparatus or process limitations (e.g., dimensions, configurations, components, process step order, etc.) can be made to further optimize the provided structures, devices and methods, as shown and described herein. In any event, the structures and devices, as well as the associated methods, described herein have many applications. Therefore, the disclosed subject matter should not be limited to any single example described herein, but rather should be construed in breadth and scope in accordance with the appended claims.

What is claimed is:

1. A vision screening device, comprising:
 a radiation source configured to emit radiation of a first wavelength;
 a sensor configured to capture radiation reflected by an eye of a patient;
 a white light source;
 a camera configured to capture a color image of the eye of the patient;
 a display unit disposed on a first side of the vision screening device and configured to display the output to an operator of the vision screening device, wherein:
  the radiation source, the sensor, the white light source and the camera are disposed on a second side of the vision screening device, opposite the first side, and
  the white light source comprises an array of light emitting diodes (LEDs) configured to illuminate the eye of the patient from a first angle, and a second angle different from the first angle, relative to an optical axis associated with the eye of the patient;
 a processor operably connected to the radiation source, the sensor, the white light source, and the camera; and
 memory storing instructions that, when executed by the processor, cause the processor to:
  cause the radiation source to emit radiation of the first wavelength during a first period of time;
  cause the sensor to capture a portion of the radiation reflected by the eye of the patient during the first period of time;
  cause the white light source to illuminate the eye of the patient during a second period of time after the first period of time;
  cause the camera to capture a color image of the eye of the patient during the second period of time;
  generate, based at least in part on a grayscale image indicative of the captured portion of the radiation and the color image, a composite image of the eye, wherein the composite image includes a first plurality of pixels representative of the grayscale image and a second plurality of pixels representative of the color image;
  determine, based on the composite image, a difference between a value associated with the eye and an expected value; and
  generate, based at least in part on the difference, an output indicative of a condition associated with the eye.

2. The vision screening device of claim 1, wherein the first wavelength is in a near-infrared (NIR) band of electromagnetic spectrum.

3. The vision screening device of claim 2, wherein the radiation source comprises an array of NIR light emitting diodes (LEDs) arranged such that a plurality of NIR LEDs share a common axis.

4. The vision screening device of claim 1, wherein the instructions further cause the processor to:

cause the white light source to illuminate the eye of the patient from the first angle during a first portion of the second period of time;

cause the camera to capture a first color image of the eye of the patient during the first portion of the second period of time;

cause the white light source to illuminate the eye of the patient from the second angle during a second portion of the second period of time;

cause the camera to capture a second color image of the eye of the patient during the second portion of the second period of time;

generate, based on the first color image and the second color image, an animated sequence of images of the eye; and display, on the display unit, the animated sequence of images.

5. The vision screening device of claim 1, wherein the instructions further cause the processor to:

cause the camera to capture a first color image of the eye of the patient corresponding to a first gaze direction of the patient;

cause the camera to capture a second color image of the eye of the patient corresponding to a second gaze direction of the patient; and generate, based on the first color image and the second color image, an image of a retina of the eye.

6. A method, comprising:

illuminating an eye of a patient during a first period of time;

capturing a grayscale image of the eye during the first period of time;

illuminating the eye during a second period of time separate from the first period of time;

capturing a color image of the eye during the second period of time;

generating, based at least in part on the grayscale image and the color image, a composite image of the eye, wherein the composite image derives a first plurality of pixel values from the grayscale image and a second plurality of pixel values from the color image;

determining, based on at least one of the color image or the composite image, a difference between a color value associated with the eye and an expected color value, wherein the eye is a first eye of the patient, and the expected color value is one of: a second color value associated with a second eye of the patient or a third color value obtained from standard data associated with human eyes; and generating, based at least in part on the difference, an output associated with the patient.

7. The method of claim 6, wherein the illumination during the first period of time comprises illuminating the eye with radiation in a near-infrared (NIR) band of electromagnetic spectrum.

8. The method of claim 6, further comprising:

determining a first area of the grayscale image corresponding to a pupil of the eye; and determining a second area of the color image corresponding to the pupil of the eye, wherein the difference is based at least in part on the first area or the second area.

9. The method of claim 6, wherein the color value is a first color value, the method further comprising:

obtaining patient data associated with the patient, wherein the patient data includes a second color value associated with the eye; and determining, as the expected color value, the second color value.

10. The method of claim 6, further comprising:

providing, as input, the grayscale image or the color image to a trained machine learning model; and receiving, from the trained machine learning model, the output.

11. The method of claim 6, further comprising:

determining that the difference is equal to or greater than a threshold value, wherein the output is based at least in part on determining that the difference is equal to or greater than the threshold value.

12. The method of claim 11, further comprising:

determining a portion of the composite image where the difference is equal to or greater than the threshold value; and generating a graphic indicating the portion of the composite image, wherein the output includes the composite image with the graphic.

13. The method of claim 12, further comprising:

providing, via a graphical user interface (GUI), the composite image with the graphic, wherein the GUI allows a user to turn the graphic on or off.

14. The method of claim 6, wherein the output is indicative of at least one of normal eye screening, additional screening required, or a disease associated with the eye.

15. A system, comprising:

memory;

a processor; and computer-executable instructions stored in the memory and executable by the processor to perform operations comprising:

causing a radiation source to emit near-infrared (NIR) radiation during a first period of time;

causing a sensor to capture a portion of the NIR radiation reflected by an eye of a patient during the first period of time;

causing a white light source to illuminate the eye during a second period of time separate from the first period of time;

causing a camera to capture a color image of the eye during the second period of time;

determining, based on the color image and the portion of the NIR radiation, a difference between a value associated with the eye and an expected value;

determining that the difference is equal to or greater than a threshold value;

generating, based at least in part on determining that the difference is equal to or greater than the threshold value, an output indicative of a condition of the eye;

causing the white light source to illuminate the eye of the patient from a plurality of angles during the second period of time;

causing the camera to capture a plurality of color images of the eye of the patient, wherein each color image of the plurality of color images corresponds to an angle of the plurality of angles;

generating, based on the plurality of color images, a video, wherein each frame of the video corresponds to a color image of the plurality of color images; and displaying, on a display screen, the video.

16. The system of claim 15, the operations further comprising:

generating a grayscale image indicative of the captured portion of the NIR radiation; and generating, based on the grayscale image and the color image, a composite image, wherein the composite image includes a first plurality of pixel values from the grayscale image and a second plurality of pixel values from the color image.

* * * * *